(12) United States Patent
Linderman et al.

(10) Patent No.: US 10,085,727 B2
(45) Date of Patent: Oct. 2, 2018

(54) VACUUM ASSISTED HANDHELD BIOPSY DEVICE

(71) Applicant: CAREFUSION 2200, INC., San Diego, CA (US)

(72) Inventors: Evan Linderman, Deerfield, IL (US); John A. Krueger, Muskego, WI (US); Phillip Qian, San Jose, CA (US); Michael Plishka, Lake Villa, IL (US)

(73) Assignee: CAREFUSION 2200, INC., San Diego, CA (US)

( * ) Notice: Subject to any disclaimer, the term of this patent is extended or adjusted under 35 U.S.C. 154(b) by 100 days.

(21) Appl. No.: 13/763,388

(22) Filed: Feb. 8, 2013

(65) Prior Publication Data

US 2014/0228705 A1  Aug. 14, 2014

(51) Int. Cl.
*A61B 10/02* (2006.01)
*A61B 10/04* (2006.01)

(52) U.S. Cl.
CPC ...... *A61B 10/0283* (2013.01); *A61B 10/0275* (2013.01); *A61B 2010/0208* (2013.01); *A61B 2010/045* (2013.01)

(58) Field of Classification Search
None
See application file for complete search history.

(56) References Cited

U.S. PATENT DOCUMENTS

| 4,445,517 | A | * | 5/1984 | Feild | A61B 10/04 600/565 |
| 4,537,182 | A | * | 8/1985 | Otani | 600/159 |
| 5,299,561 | A | * | 4/1994 | Yoshimoto | A61B 1/00068 600/159 |
| 5,335,671 | A | * | 8/1994 | Clement | A61B 10/04 600/566 |
| 5,951,489 | A | * | 9/1999 | Bauer | 600/567 |
| 6,540,713 | B1 | | 4/2003 | Cimino | |

(Continued)

FOREIGN PATENT DOCUMENTS

WO  WO 2011/046722 A1  4/2011

OTHER PUBLICATIONS

International Search Report and Written Opinion, U.S. Patent Application No. PCT/US14/14644 dated Apr. 23, 2014.
(Continued)

*Primary Examiner* — Matthew Kremer
(74) *Attorney, Agent, or Firm* — Arent Fox LLP

(57) ABSTRACT

A vacuum assisted handheld biopsy device includes a housing, a stylet slideable within a cannula, the stylet having a hollow tube portion and a tissue collection portion coupled together, an actuator slideable within the housing for driving at least one of the stylet and the cannula, a vacuum source in communication with the stylet, and an ambient air opening in selective communication with the vacuum source. The coupling of the hollow tube portion with the tissue collection portion provides a fluid flow path sufficient to provide a vacuum suction to the tissue collection portion. A stylet for a vacuum assisted handheld biopsy device includes a hollow tube portion and a tissue collection portion coupled together. The coupling of the hollow tube portion and the tissue collection portion provides a fluid flow path sufficient to provide a vacuum suction to the tissue collection portion.

16 Claims, 55 Drawing Sheets

(56) References Cited

U.S. PATENT DOCUMENTS

| | | |
|---|---|---|
| 8,002,713 B2 | 8/2011 | Heske et al. |
| 8,267,868 B2 | 9/2012 | Taylor et al. |
| 2003/0216667 A1* | 11/2003 | Viola ................. A61B 10/0275 600/564 |
| 2007/0149893 A1* | 6/2007 | Heske ................ A61B 10/0275 600/566 |
| 2007/0179401 A1* | 8/2007 | Hibner .......................... 600/567 |
| 2010/0106055 A1* | 4/2010 | Heske ................ A61B 10/0233 600/566 |
| 2010/0312140 A1 | 12/2010 | Smith et al. |
| 2011/0190814 A1* | 8/2011 | Mark ............................ 606/214 |
| 2011/0208086 A1 | 8/2011 | Hibner et al. |
| 2012/0022397 A1* | 1/2012 | Jarial ........................... 600/567 |

OTHER PUBLICATIONS

Extended European Search Report of related European Patent Application No. 14749046.0 dated Aug. 30, 2016.

\* cited by examiner

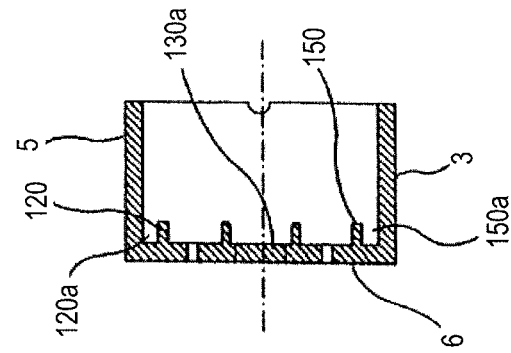
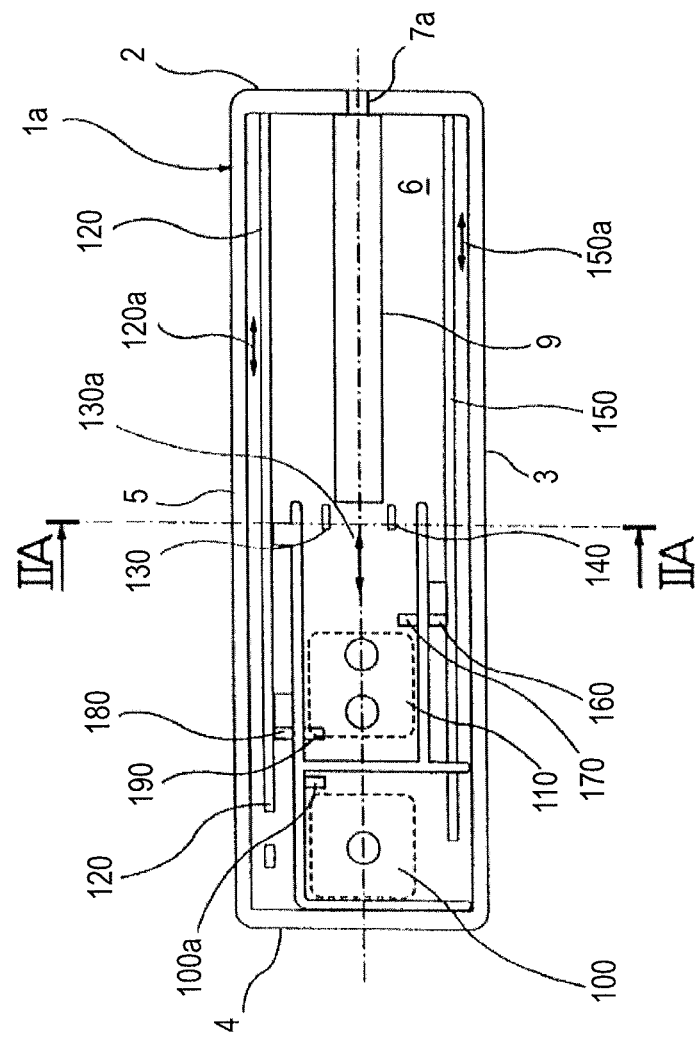

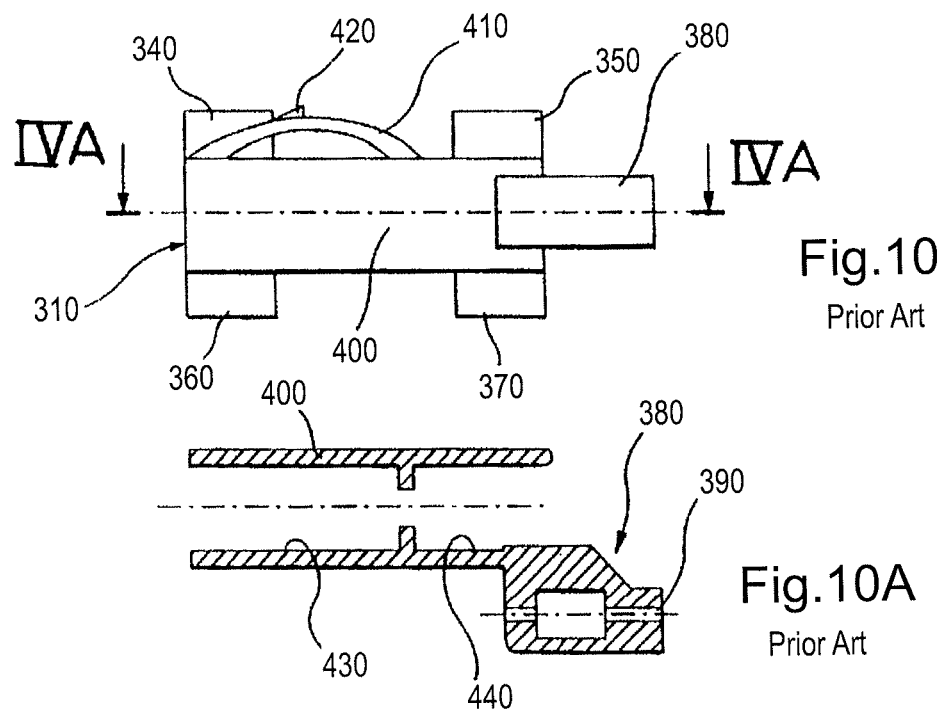
Fig. 10 Prior Art
Fig. 10A Prior Art
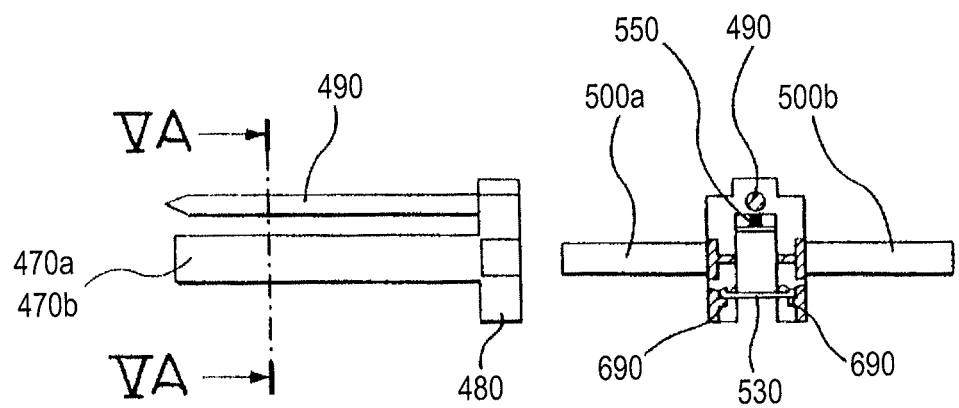
Fig. 11 Prior Art
Fig. 11A Prior Art

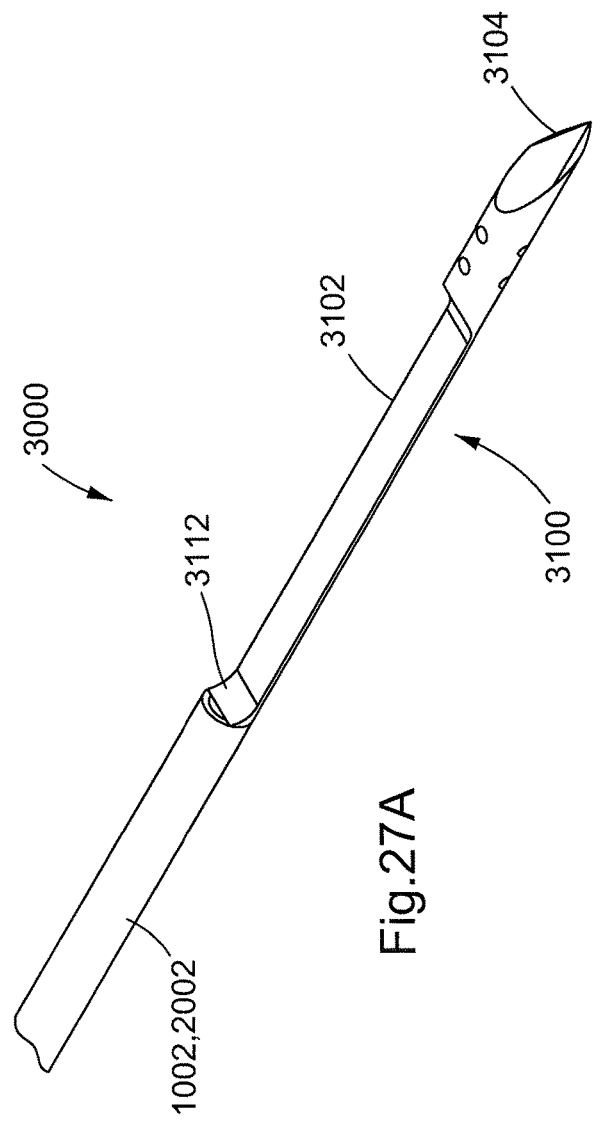
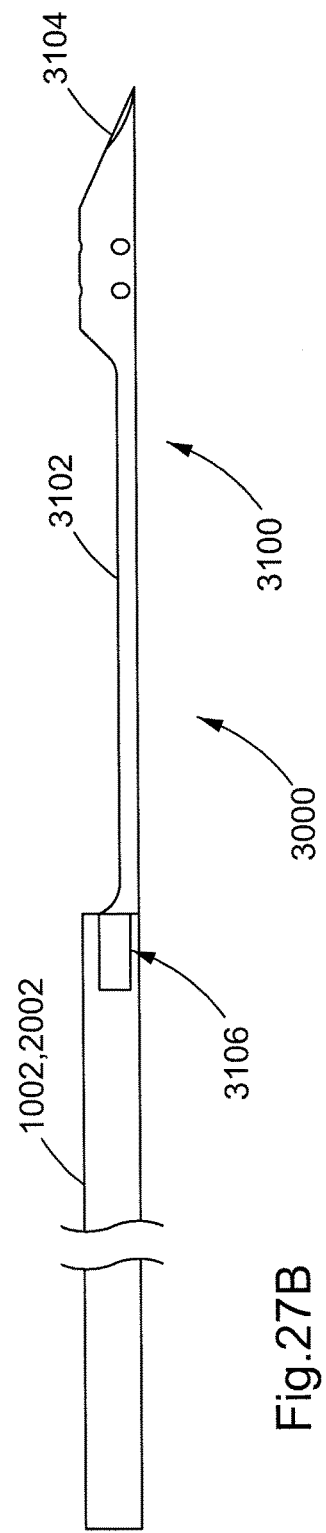
Fig.27A
Fig.27B

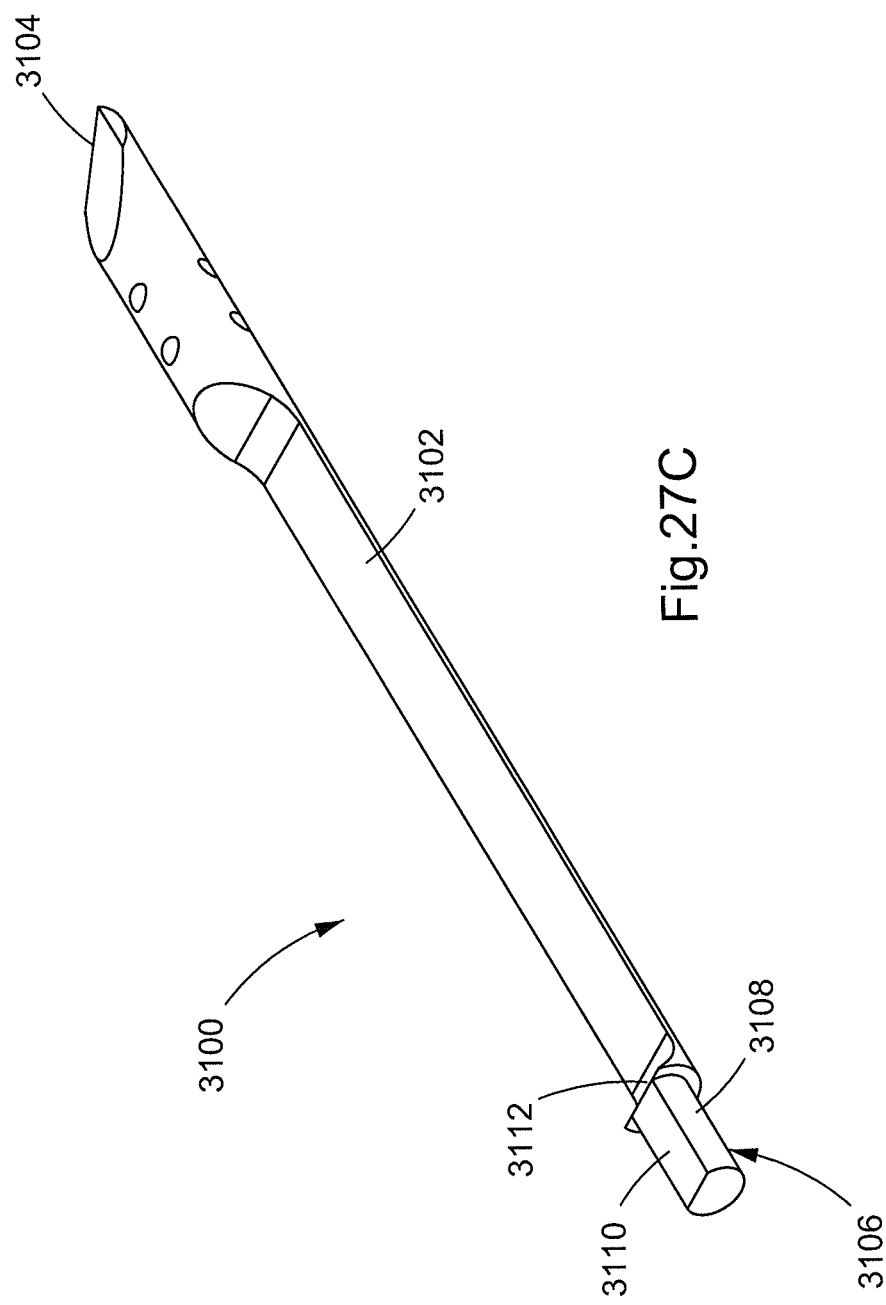

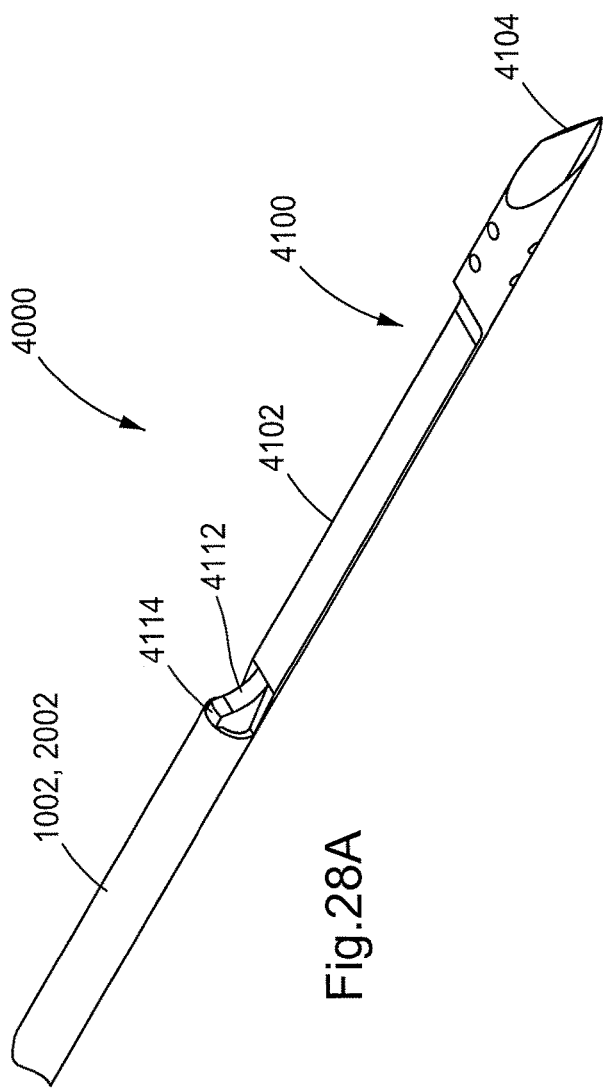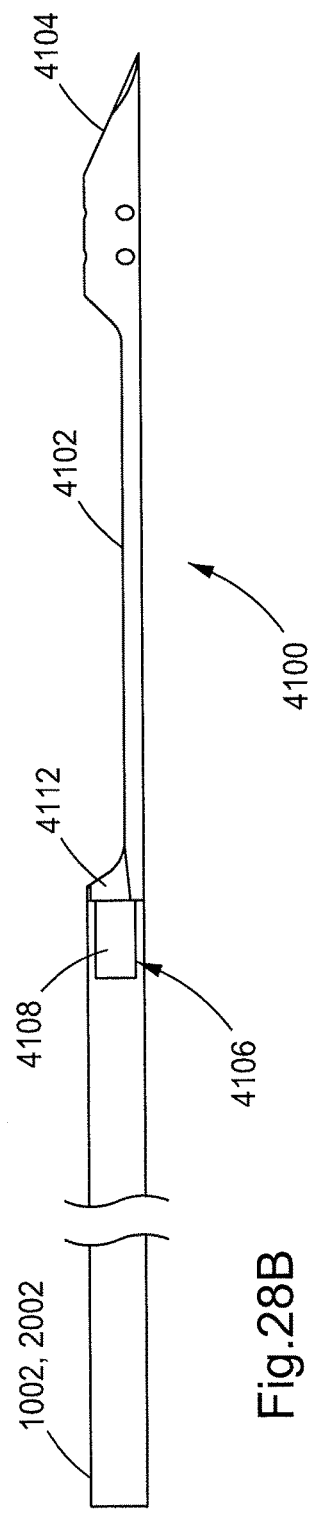
Fig.28A
Fig.28B

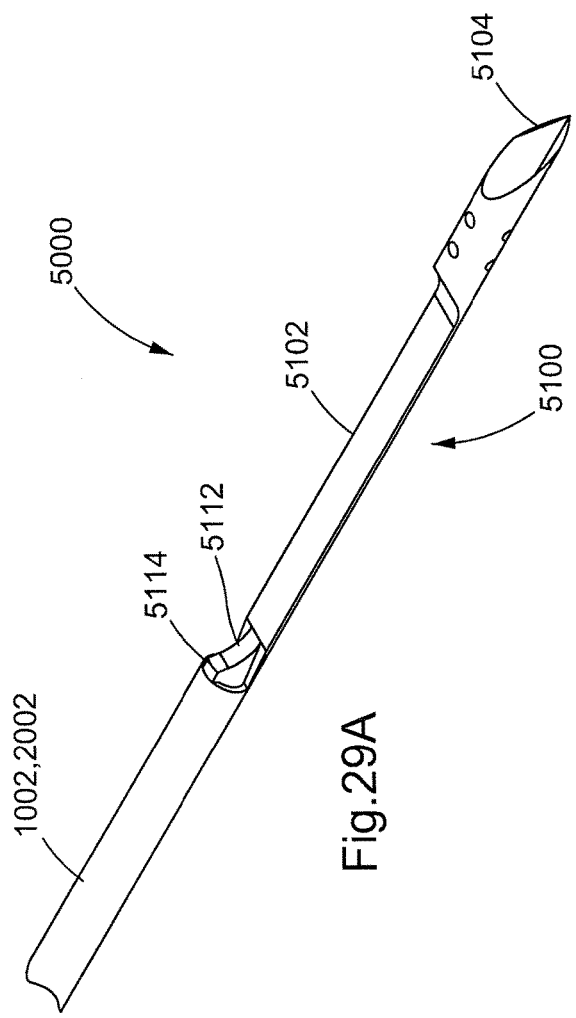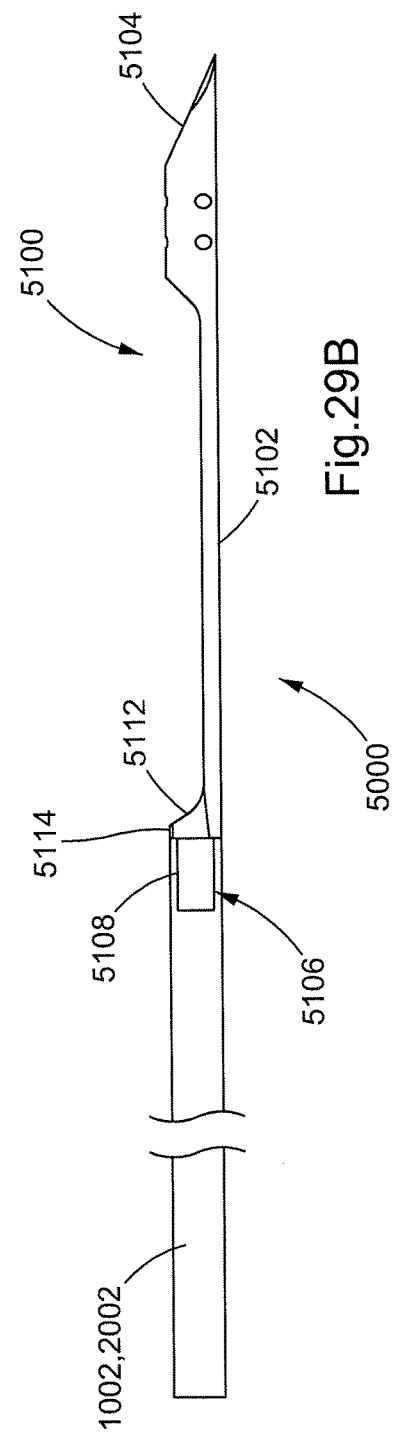

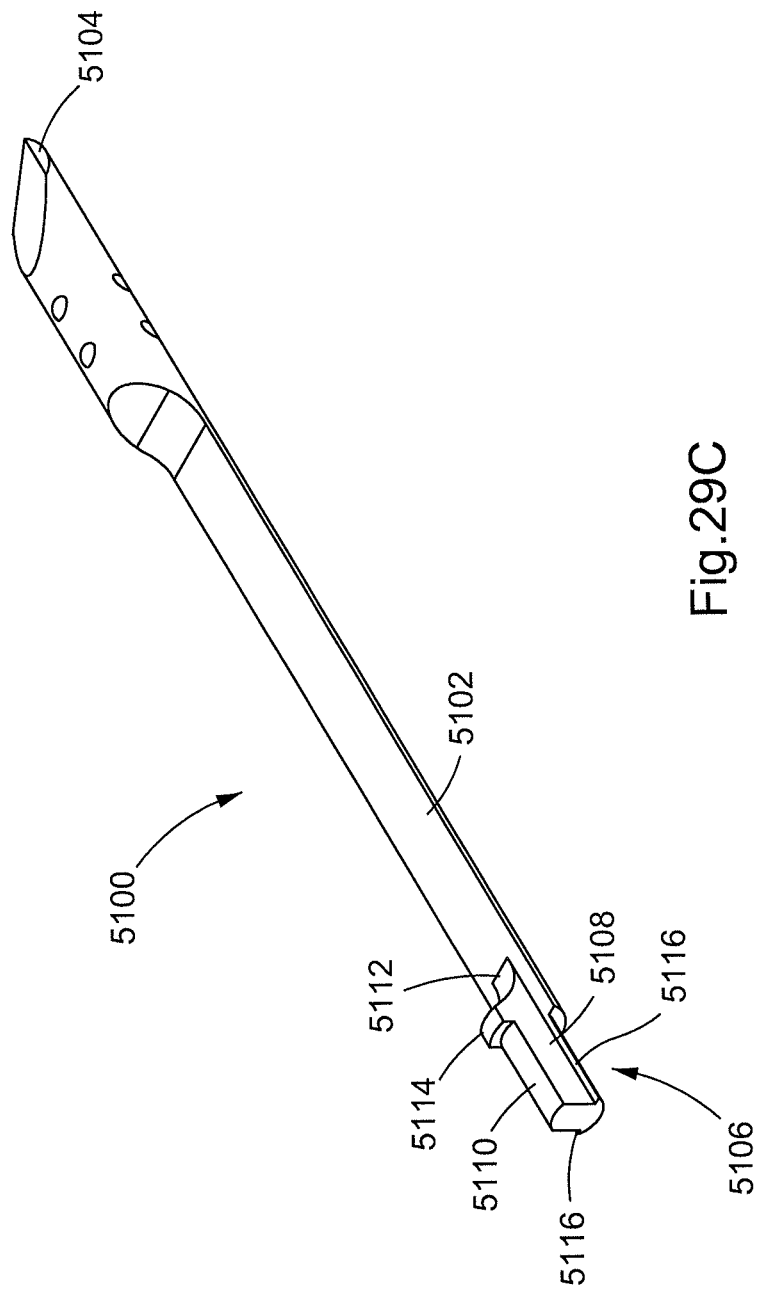

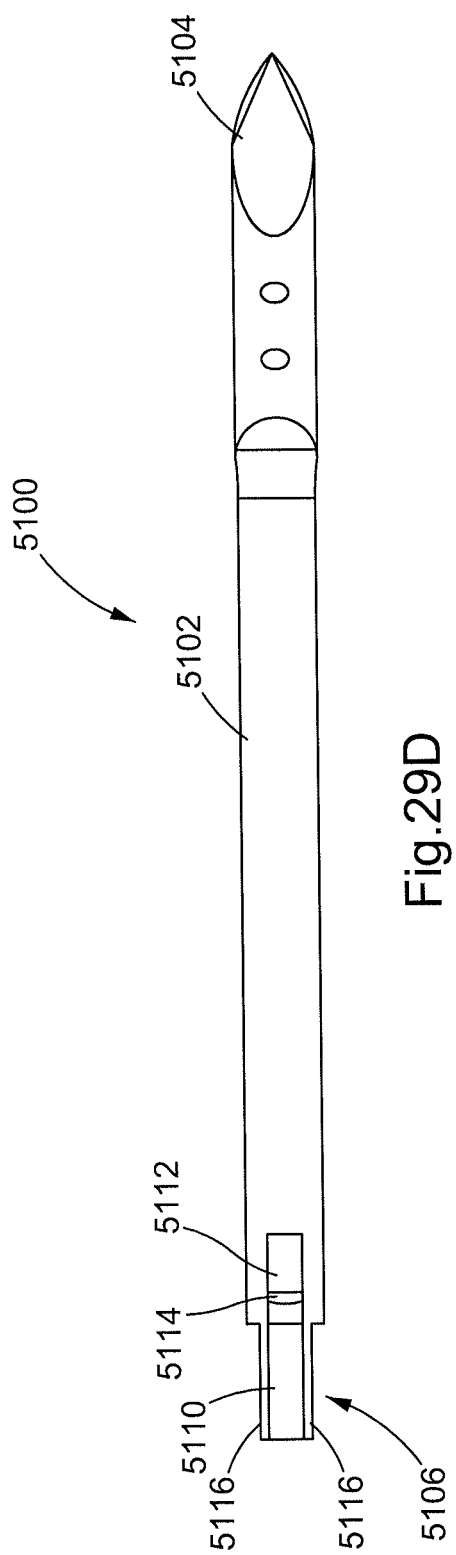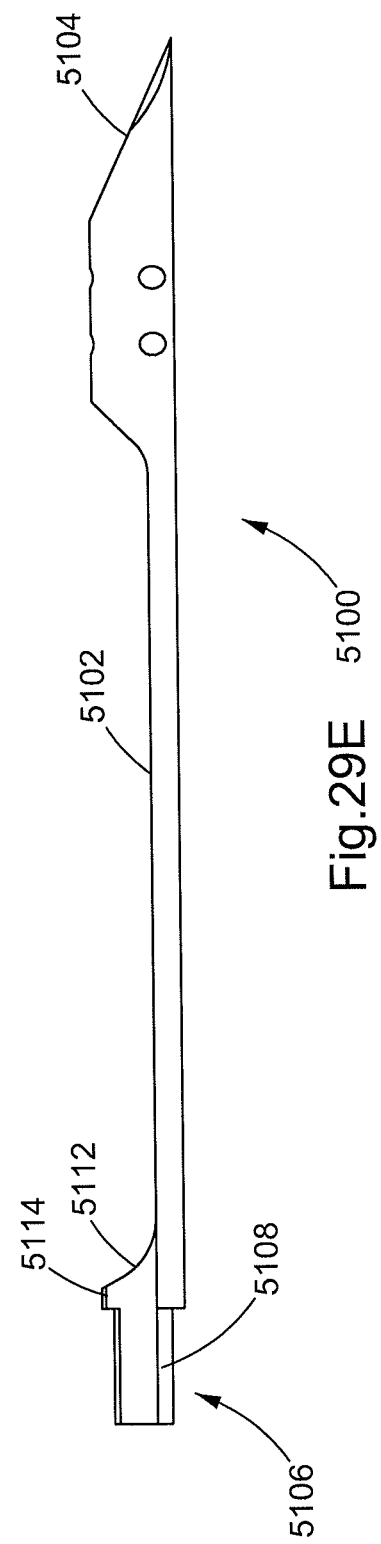
Fig.29D
Fig.29E

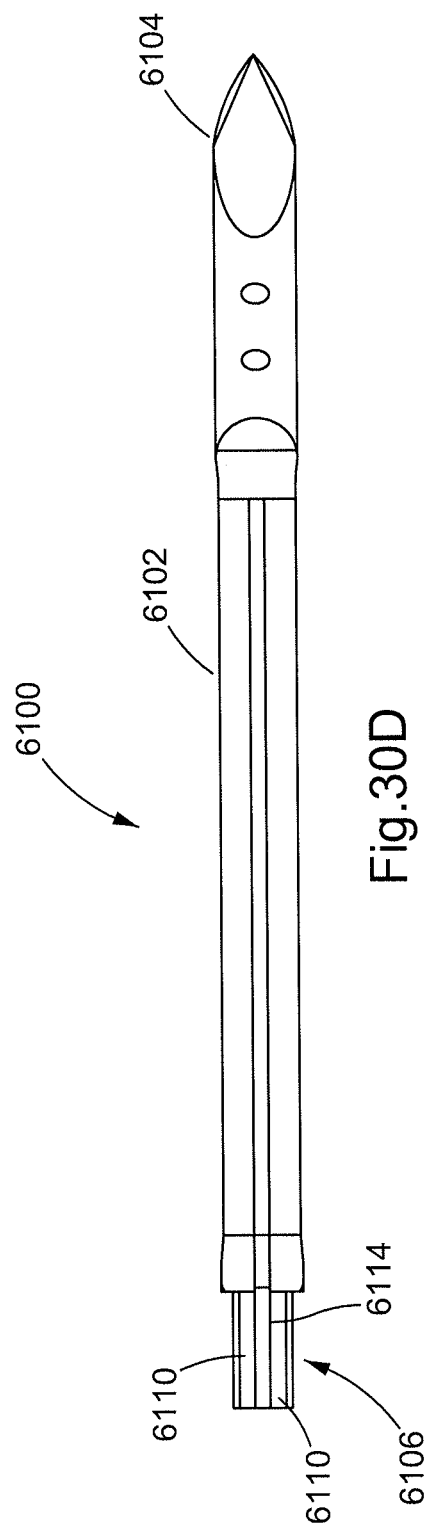
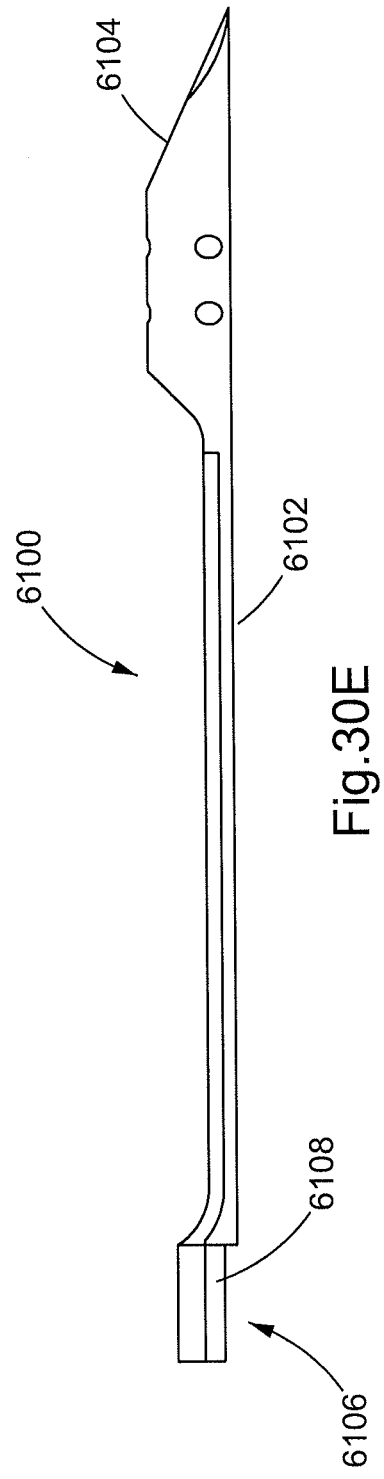

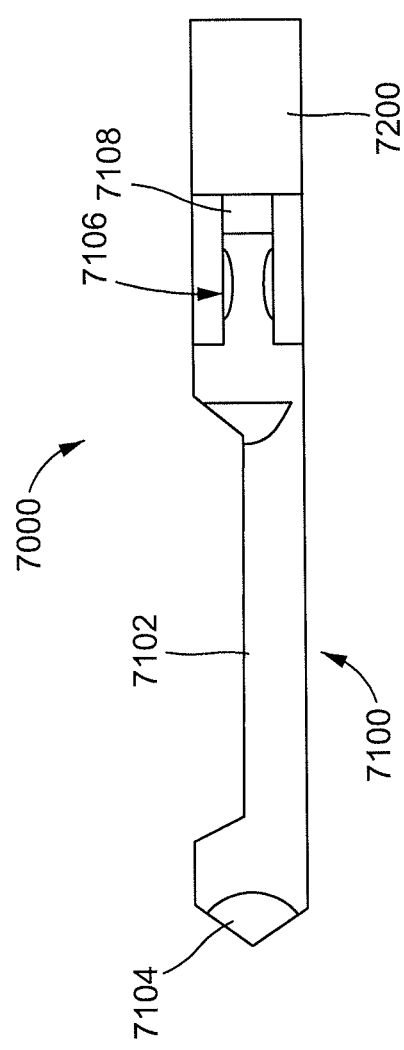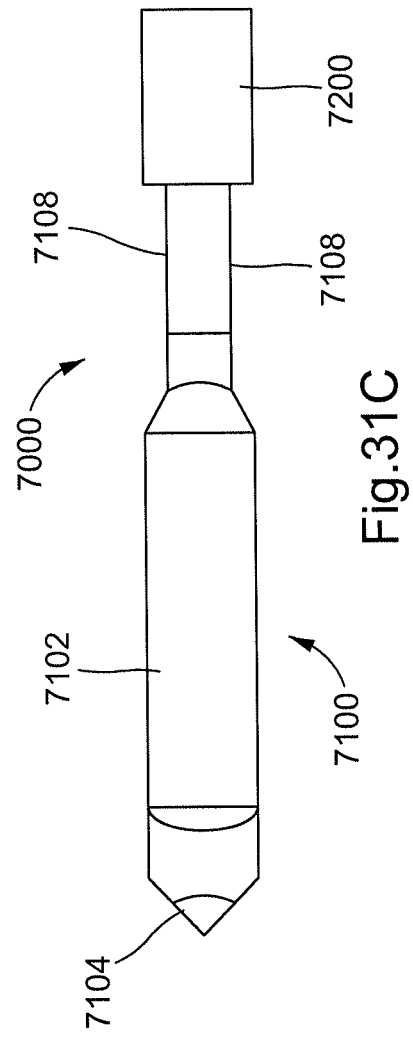

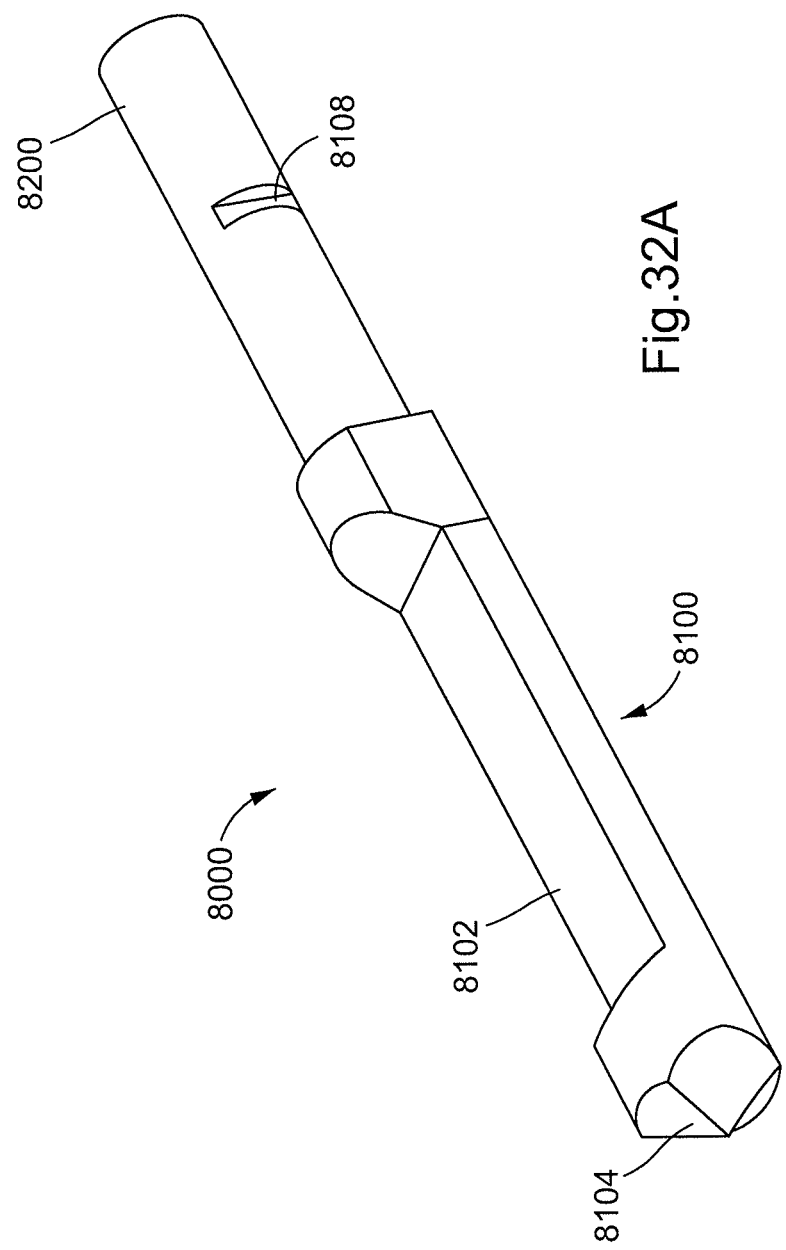

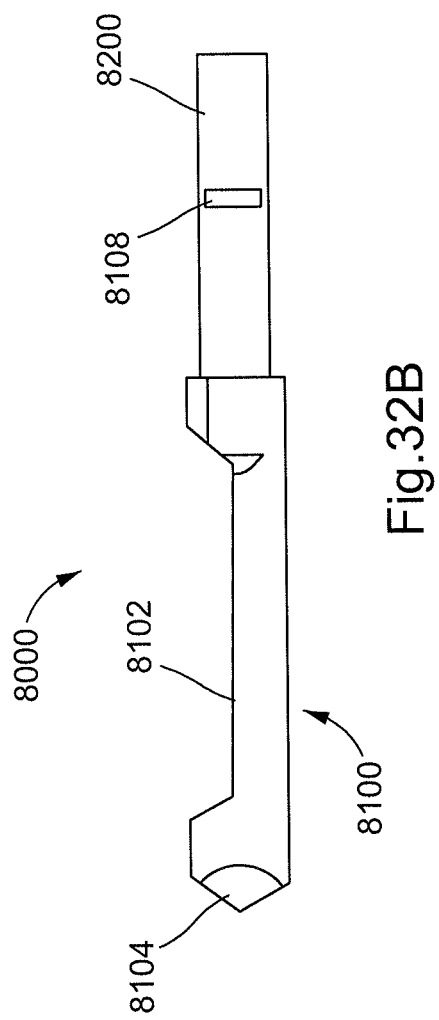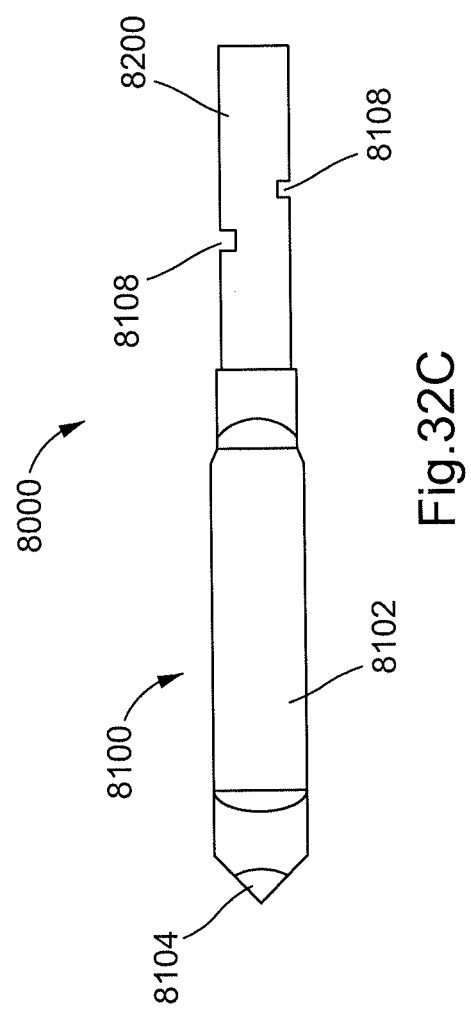

VACUUM ASSISTED HANDHELD BIOPSY DEVICE

BACKGROUND OF THE INVENTION

Field of the Invention

Aspects of the present invention relate in general to biopsy devices, and more particularly to handheld biopsy devices.

Background

Biopsy needle devices with handpieces containing an actuating apparatus which activates the motion of a biopsy needle are known. For example, U.S. Pat. No. RE38,776 to Bauer discloses a biopsy surgical appliance comprises a biopsy needle having a stylet and a cannula, disposed coaxially along an axis and activated by a mechanical device with two slides which can slide longitudinally inside a shell. The first slide of the two slides has a "U" shape with tines oriented longitudinally and is moved longitudinally in a first operative environment, in which the central section of the "U" shape supports one component of two components which constitute the biopsy needle. The second slide of the two slides has a head which extends towards and beyond the axis without interfering with the first operative environment and is inserted freely between the tines of the first slide, and in which the head supports the other component of the two components which constitute the biopsy needs. U.S. Pat. No. 5,951,489 to Bauer discloses a biopsy surgical appliance includes a stylet slider sliding in a longitudinal plane and placed laterally with respect to a longitudinal axis, a cannula slider sliding in a longitudinal plan placed laterally with respect to the axis of a needle and not interfering in the operative framework of stylet slider, holding/releasing device made up of a first independent hooking/releasing device for stylet slider, a second independent hooking/releasing device for cannula slider, two independent single control push-buttons of which the first one acts on the first hooking/releasing device and the second one is of the progressive type and acts in progression on said first hooking/releasing device at the first device if it has not been released yet and then on the second hooking/releasing device.

Biopsy needle devices having vacuums to assist is obtaining a sample are also known. For example, U.S. Pat. No. 5,526,822 to Burbank et al. discloses a method and device for the automated biopsy and collection of soft tissue having a piercing needle with a receiving port to trap tissue prior to cutting. A motor drive directs and positions the tissue receiving port at a lesion site in arbitrary positions about and along the longitudinal axis of the device. A cutter advances into the receiving chamber and severs tissue which has prolapsed into the receiving port. The severed tissue is then removed from the receiving port without removing the piercing needle receiving port from the lesion site. A tissue sample cassette provides storage for the samples as well as a means for coding and decoding the location from which the samples were obtained. After the piercing needle has been positioned within the tissue, when it is desired to obtain a tissue sample, a control unit actuates a vacuum source which is applied to a vacuum connection of the device, thereby generating a region of low pressure within the piercing, needle. The low pressure created by the vacuum source facilitates the prolapse of tissue into the piercing needle.

However, U.S. Pat. Nos. RE38,776 and 5,951,489, while being compact handheld devices capable of obtaining a precise sample with a smaller, less invasive needle, there is no vacuum assistance. These devices often do not collect a sufficient amount of tissue. While U.S. Pat. No. 5,526,822 includes vacuum assistance, the device is cumbersome and requires a relatively large needle to allow the vacuum to operate. Thus, there remains a need for a handheld biopsy device with a smaller, less invasive needle, having vacuum assistance to obtain a tissue sample.

SUMMARY OF THE INVENTION

Aspects of the present invention provide, among other things, a biopsy device comprising a vacuum assisted handheld biopsy device comprising a housing; a stylet slideable within a cannula, the stylet having a hollow tube portion and a tissue collection portion coupled together; an actuator slideable within the housing for driving at least one of the stylet and the cannula; a vacuum source in communication with the stylet; and an ambient air opening in selective communication with the vacuum source, wherein the coupling of the hollow tube portion and the tissue collection portion provides a fluid flow path sufficient to provide a vacuum suction to the tissue collection portion.

In one example variation the ambient air opening is located on the actuator.

In another example variation the device includes a pushbutton that releases at least one of the stylet and cannula from a preloaded state, and the ambient air opening is located on the pushbutton.

In a variation, the tissue collection portion comprises a ramp abutting the hollow tube portion, and the fluid flow path is at least partially defined by the ramp. In an aspect the ramp In another variation tissue collection portion is coupled to the hollow tube portion via an insertion member. The insertion member comprises a curved portion and a flat portion, the curved portion is bonded to an inside surface of the hollow tube portion, and a space between the flat portion and the inside surface of the hollow tube portion at least partially defines the fluid flow path.

In still another variation the insertion member comprises a opposing curved portions and opposing flat portions, the curved portions are bonded to an inside surface of the hollow tube portion, and a space between the flat portions and the inside surface of the hollow tube portion at least partially defines the fluid flow path.

In yet another variation the insertion member comprises a curved portion bonded to an inside surface of the hollow tube portion, and an open passageway at least partially defining the fluid flow path.

Another variation includes a method of operating the vacuum assisted handheld biopsy device, the method comprising preloading the device by pulling the actuator in a direction away from the tissue collection portion; activating the vacuum source; and closing the ambient air opening, wherein closing the ambient air opening directs a vacuum along the fluid flow path.

In another variation, the method further includes releasing at least one of the stylet and cannula from a preloaded state contemporaneously with closing the ambient air opening.

Another aspect of the invention includes a stylet for a vacuum assisted handheld biopsy device, the stylet comprising a hollow tube portion and a tissue collection portion coupled together, wherein the insertion member provides a fluid flow path sufficient to provide a vacuum suction to the tissue collection portion.

Additional advantages and novel features of various aspects of the present invention will be set forth in part in the description that follows, and in part will become more apparent to those skilled in the art upon examination of the following or upon learning by practice thereof.

BRIEF DESCRIPTION OF THE FIGURES

In the drawings:

FIG. 8 is a bottom view of the appliance shown in FIG. 7;

FIG. 8A is a sectional view along line IIA-IIA of FIG. 2;

FIG. 10 is a side view of the appliance illustrated in FIG. 7;

FIG. 10A is a sectional view along lines IVA-IVA of FIG. 10;

FIG. 11 is a plan view of a component of the device of FIGS. 7, 1A and 7B;

FIG. 11A is a section along line VA-VA of FIG. 11;

FIGS. 27A is a partial perspective view of a stylet in accordance with aspects of the present invention;

FIG. 27B is a side view of the stylet of FIG. 27A;

FIG. 27C is a perspective view of the tissue collection portion of the stylet of FIG. 27A;

FIGS. 28A is a partial perspective view of a stylet in accordance with other aspects of the present invention;

FIG. 28B is a side view of the stylet of FIG. 28A;

FIGS. 29A is a partial perspective view of a stylet in accordance with other aspects of the present invention;

FIG. 29B is a side view of the stylet of FIG. 29A;

FIG. 29C is a perspective view of the tissue collection portion of the stylet of FIG. 29A;

FIG. 29D is a top view of the tissue collection portion of the stylet of FIG. 29A;

FIG. 29E is a side view of the tissue collection portion of the stylet of FIG. 29A;

FIG. 30D is a top view of the tissue collection portion of the stylet of FIG. 30A;

FIG. 30E is a side view of the tissue collection portion of the stylet of FIG. 30A;

FIG. 31B is a side view of the stylet of FIG. 31A;

FIG. 31C is a top view of the stylet of FIG. 31A;

FIG. 32A is a partial perspective view of a stylet in accordance with other aspects of the present invention;

FIG. 32B is a side view of the stylet of FIG. 32A; and

FIG. 32C is a top view of the stylet of FIG. 32A.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

The Prior Art Devices

As will be discussed in more detail below, the aspects of the present invention include improvements on known handheld biopsy devices. Therefore, it is useful to first describe the structure and operation of the known handheld biopsy devices. The internal structure and operation of the example inventive handheld biopsy devices are the same as shown and described in this section. For clarity, only the features unique to the inventive handheld biopsy devices are discussed when describing the inventive handheld biopsy devices. It should be appreciated that the prior art devices shown and described in detail herein are only two examples of prior art devices to which the inventive aspects may be applied. Other, non-limiting examples of prior art devices to which the inventive aspects may be applied include: U.S. Pat. Nos. 5,916,175, 6,120,463, and 6,749,576, each of which is hereby incorporated by reference herein.

Figure 1:
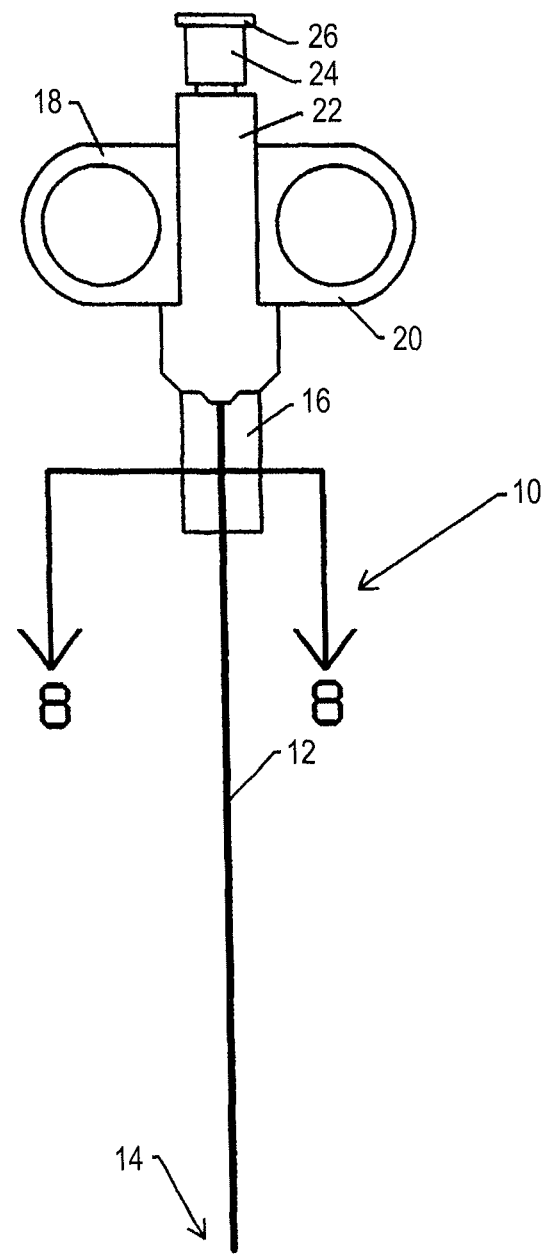
FIG. 1 is a plan view of a prior art surgical instrument employing the present invention.

U.S. Pat. No. RE38,776 (hereinafter, "the '776 patent"), which is expressly incorporated by reference herein, discloses a handheld biopsy device without vacuum assistance. FIGS. 1-6 illustrate the biopsy device of the '776 patent. FIG. 1 is a frontal plan view of a biopsy needle. To be inserted into the patient is long thin stainless steel cannula 12. Although not seen in this view, cannula 12 is hollow, having a central lumen containing a longitudinally slideable stylet which is described in greater detail below. Distal tip 14 which is described in greater detail below and shown in close up in FIG. 4.

The proximal end of cannula 12 is coupled to preloading engagement assembly 16 to permit retraction and advancement of cannula 12 with respect to main housing 22, which is preferably molded of a suitable polymer for disposability. Before insertion, the surgical instrument is preloaded by manually pulling actuation button 24 proximally of main housing 22 until engagement of the preloading engagement assembly 16 is achieved for the desired tissue sample size.

The preloaded surgical instrument 10 is grasped by the attending medical person using a single hand. The index finger is placed in finger hold 20 and the middle finger is placed in finger hold 18. Distal tip is advanced into the patient to the tissue sample site. After distal tip 14 is located at the tissue sample site, thumb surface 26 is pressed to carefully advance actuation button 24 distally. This is done carefully to avoid applying sufficient force to disengage preloading engagement assembly 16. This advances the distal tip of the stylet (not shown), which passes through grommet 28, past the tissue sample site exposing the tissue sample notch of the selected size (i.e. size preloaded). Further pressure is exerted on thumb surface 26 to disengage preloading engagement assembly 16. This permits the spring (not shown), which was compressed during the preloading procedure, to drive the sharpened distal tip of cannula 12 in the distal direction to excise the tissue sample and encase it between the tissue sample notch and the inner wall of cannula 12. Surgical instrument 10 is removed, and the tissue sample it contains is removed and analyzed.

Figure 2:
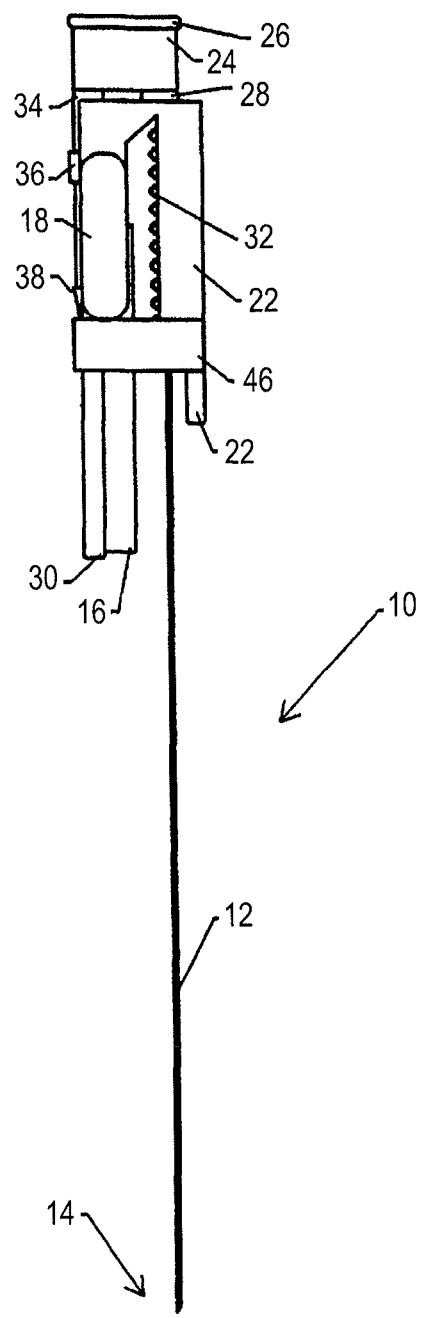
FIG. 2 is a side view of the prior art surgical instrument of FIG. 1.

FIG. 2 is a side view of surgical instrument 10. Preloading engagement assembly 16 is slideably contained within engagement track 30, which is fixedly attached and preferably molded as part of housing 22. A tab of preloading engagement assembly 16, obscured in the view by fixed strut 46 and housing 22, is fixedly coupled to the proximal end of cannula 12 and impinges on the distal end of compression spring 32. Therefore, as preloading engagement assembly 16 slides proximally within engagement track 30, cannula 12 moves in a proximal direction and compression spring 32 is further compressed.

During the preloading procedure, actuation button 24 is pulled proximally with regard to housing 22. As a result, preloading engagement assembly 16 is pulled proximally within engagement track 30 by preloading strut 34. In accordance with the above explanation, this tends to further compress compression spring 32 and to move cannula 12 in a proximal direction. Engagement latch 38 latches preloading engagement assembly 16 in one of many possible positions (i.e. selections of the tissue sample size). Compression spring 32 tends to keep preloading engagement assembly 16 in the selected position by the distal force of its compression. Fixed strut 36, which is preferably molded as a portion of housing 22, maintains the position of preloading strut 34.

Figure 3A:
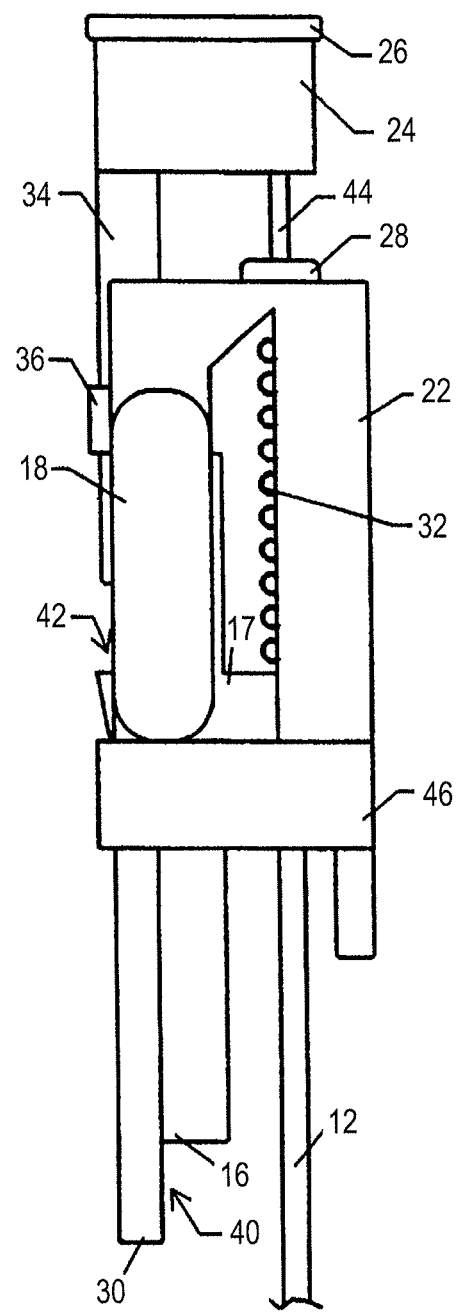
FIG. 3A is a prior art partial side view preloaded for the smallest tissue sample size.

FIG. 3A is a partial side view showing surgical instrument 10 preloaded for the smallest tissue sample size. Preloading engagement assembly 16 has been slid proximally the distance 40, exposing a partial view of tab 17, which is preferably molded as a portion of preloading engagement assembly 16. It is latched by engagement latch 38 at corresponding distance 42. In the preloaded state, the proximal end of stylet 44 can be seen protruding from grommet 28 and attached to actuation button 24. All other referenced elements are as previously described.

Figure 3B:
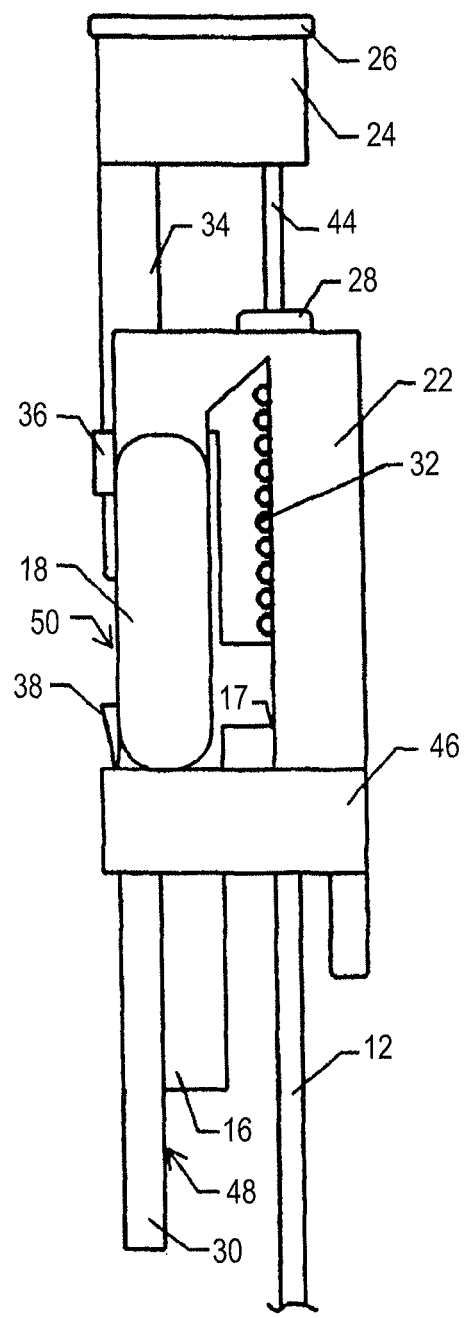
FIG. 3B is a prior art partial side view preloaded for the intermediate tissue sample size.

FIG. 3B is a partial side view, similar to FIG. 3A, showing surgical instrument 10 preloaded to an intermediate tissue sample size. Distance 48 is greater than distance 40 (see also FIG. 3A) and directly corresponds to distance 50. Also show is a larger view of tab 17 of preloading engagement assembly 16.

Figure 3C:
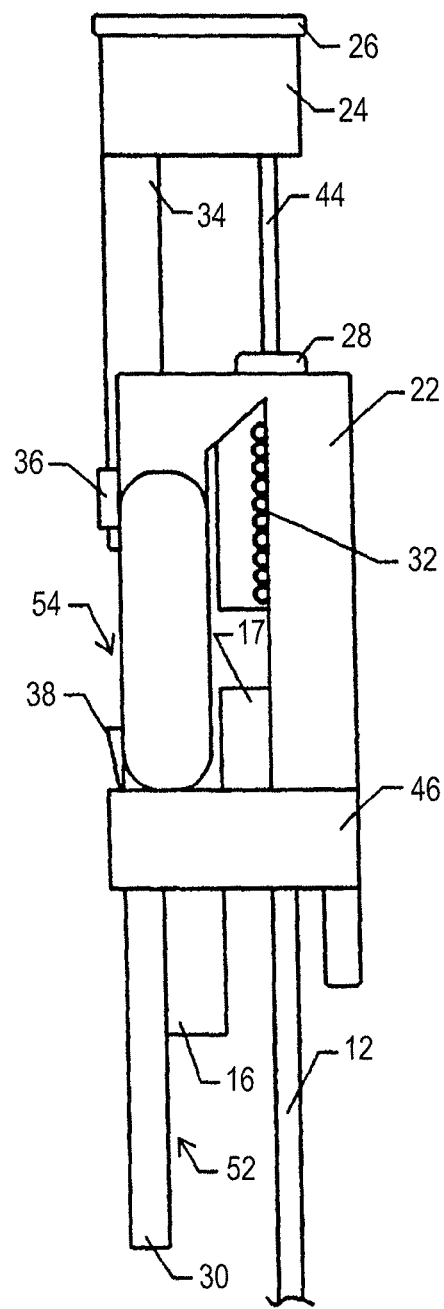
FIG. 3C is a prior art partial side view preloaded for the largest tissue sample size.

FIG. 3C is a partial side view, similar to FIG. 3B, showing surgical instrument 10 preloaded to the largest tissue sample size. Distances 52 and 54 are at a maximum. All other referenced elements are as previously described.

Figure 4:
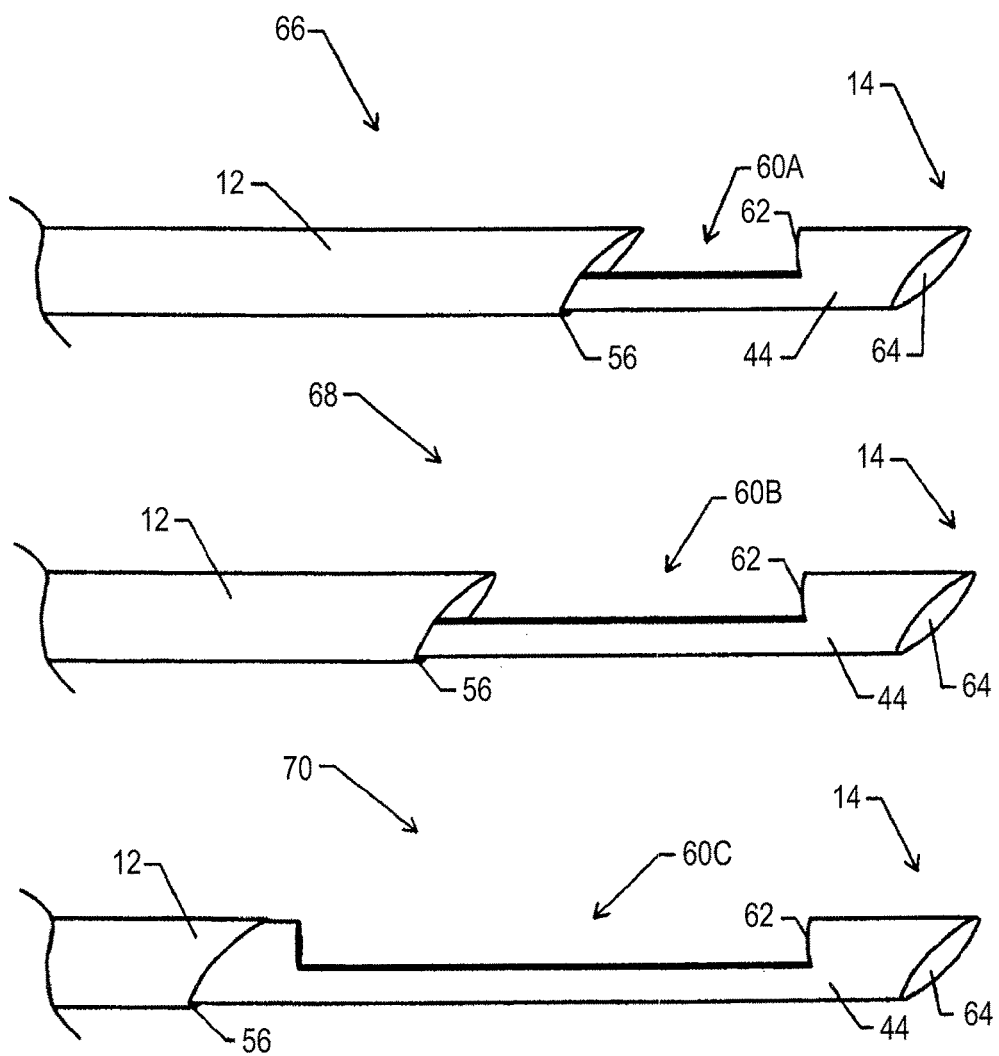
FIG. 4 is a prior art cut away close up view of the distal tip showing the tissue sample notch preloaded for the three different tissue sample sizes.

FIG. 4 shows three close up view of distal tip 14. View 66 corresponds to preloading of the device for the smallest tissue sample size 60A with stylet 44 advanced to the distal most position for exposure of the tissue sample notch.

View 68 shows stylet 44 advanced distally after preloading to intermediate tissue sample size 60B. Similarly, view 70 shows largest tissue sample size 60C.

For each of these configurations, the tissue sample present within the tissue sample notch is excised by sharpened edge 56 of cannula 12 as compression spring 32 drives cannula 12 distally over stylet 44 upon disengagement of preloading engagement assembly 16 (see also FIGS. 1-3C). In the completely disengaged position, cannula 12 preferably covers stylet 44 completely, thus encasing the excised tissue sample.

Distal end 64 of stylet 44 is ground to an elliptical shape in a plane directed away from distal end 62 of the tissue notch. This permits the distance from distal edge 62 to the most distal point of stylet 44 to be minimized for a given rigidity of the distal end of stylet 44, because it maximizes the distance from distal edge 62 to distal end 64. Minimizing the distance from distal edge 62 to the most distal point of stylet 44 tends to limit the trauma to the patient because it minimizes the distance beyond the tissue sample which must be pierced by stylet 44 (i.e. the distance from distal end 62 to the most distal point of distal end 64). Further rigidity is achieved by grinding sharpened edge 56 in the same plane as distal end 64.

Figure 5:
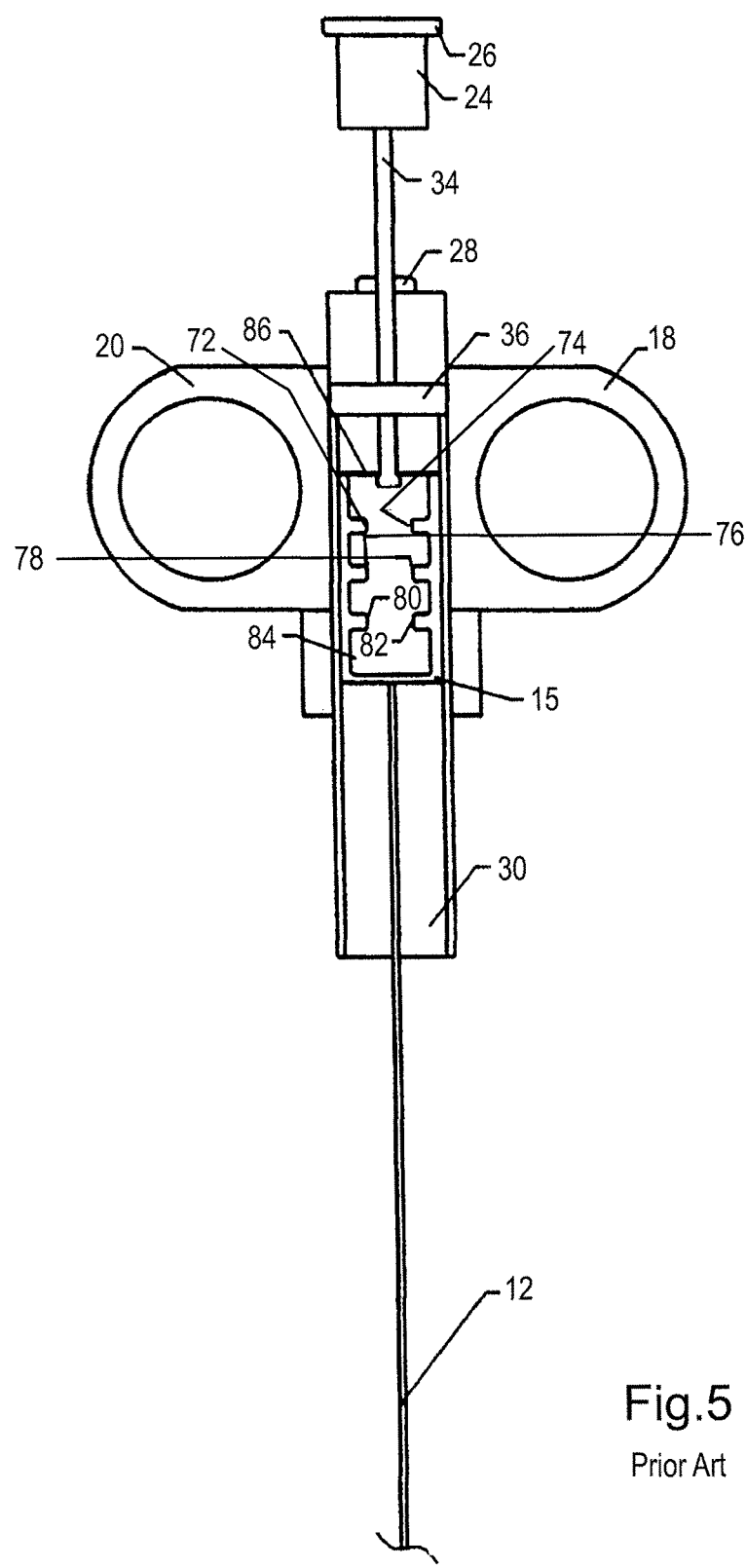
FIG. 5 is a prior art partially cut away rear view showing the means for preloading for different tissue sample sizes.

FIG. 5 is a rear view of surgical instrument 10 preloaded to the largest tissue sample size with engagement latch 38 and a portion of engagement track 30 removed to show details of preloading engagement assembly 16. A portion of the rear of preloading engagement assembly 16 is concavely recessed creating general recess 84. This recess permits advancement of engagement strut 34 distally to advance stylet 44 distally of cannula 12 to expose the tissue sample notch to the tissue sample (see also FIG. 4). However, proximal movement of engagement strut 34 engages preloading stop 86 to permit preloading.

General recess 84 contains stop members 72 and 74 for the smallest tissue sample size; stop members 76 and 78 for the intermediate tissue sample size; and stop members 80 and 82 for the largest tissue sample size. These stop members latch against engagement latch 38 (see also FIG. 3A-3C) to maintain the preselected tissue sample size. However, engagement strut 34 is free to move distally of stop members 72, 74, 76, 78, 80, and 82 within general recess 84 to permit advancement of stylet 44 distally of cannula 12 (see also FIG. 4).

Figure 6:
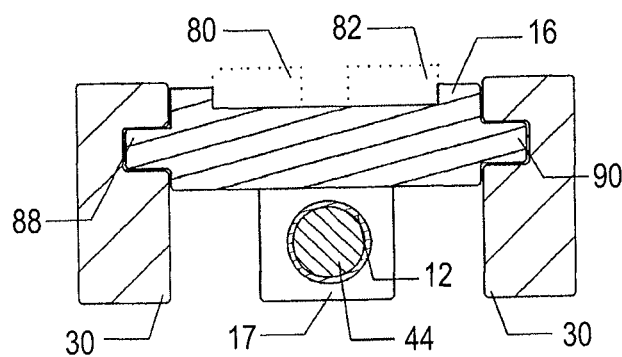
FIG. 6 is a prior art sectioned partial view of the preloading engagement means.

FIG. 6 is a partial sectioned view of preloading engagement assembly 16 taken along 8-8 in FIG. 1. Projections 88 and 90 of preloading engagement assembly 16 slide within corresponding recesses within engagement track 30. All other referenced elements are as previously described. Preferably cannula 12, stylet 44 and compression spring 32 are fabricated of stainless steel and all other elements are molded of a convenient disposable polymer.

Figure 7:
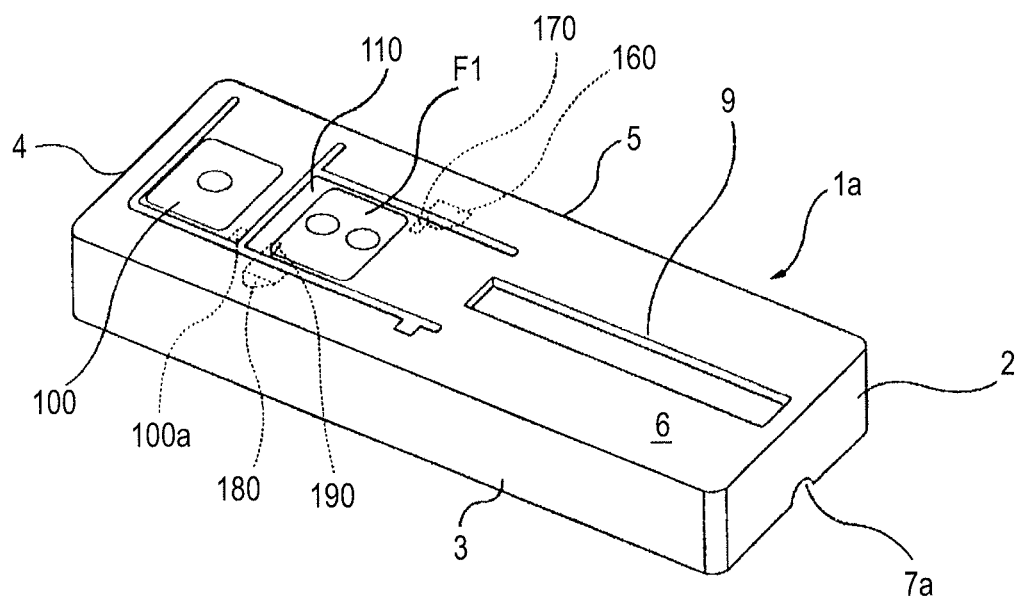
FIG. 7 is a perspective view illustrating the upper part of a prior art biopsy surgical appliance object with the lower part being shown elsewhere.
Figure 7A:
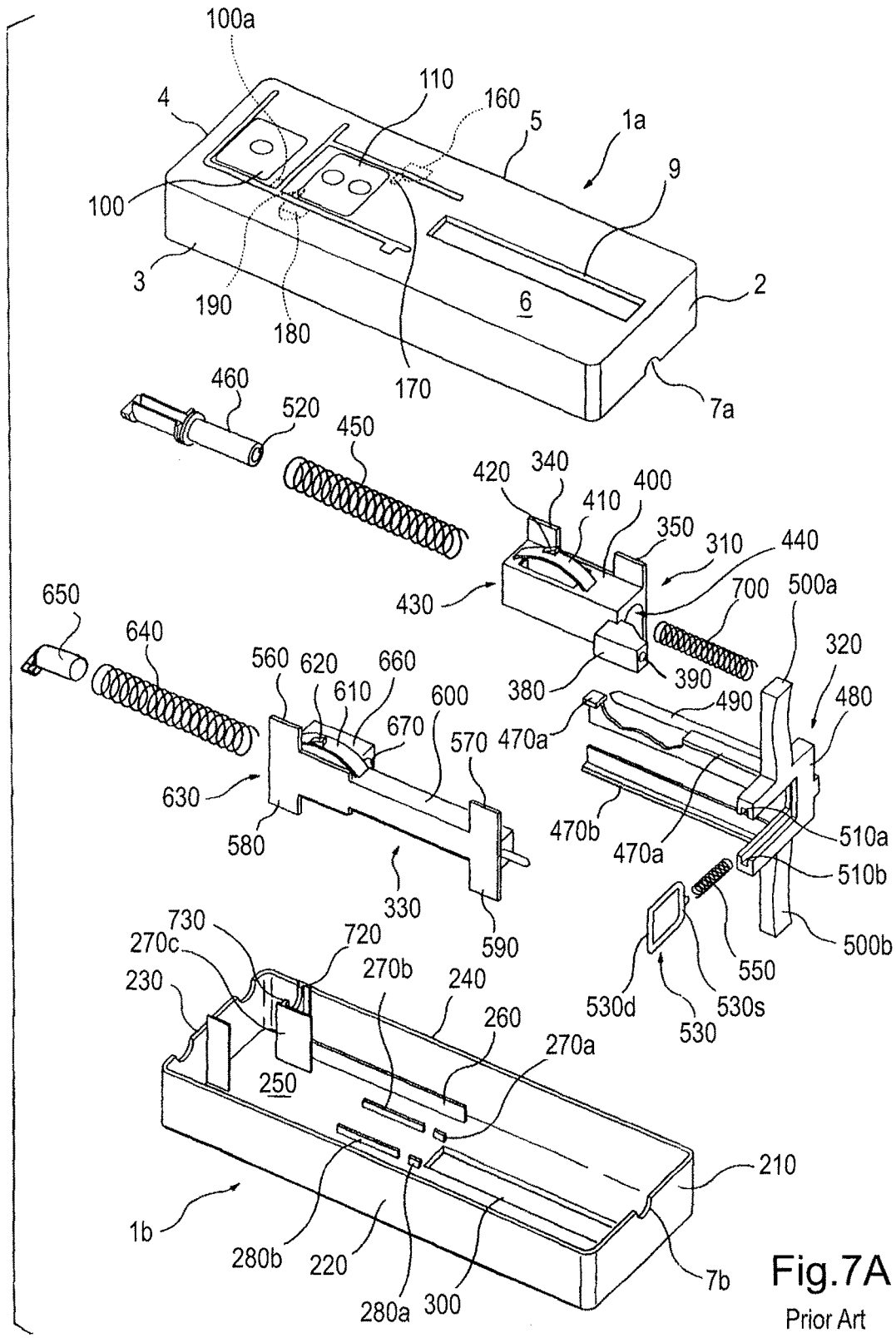
FIG. 7A is an exploded perspective view illustrating components of biopsy surgical appliance of FIG. 7.
Figure 7B:
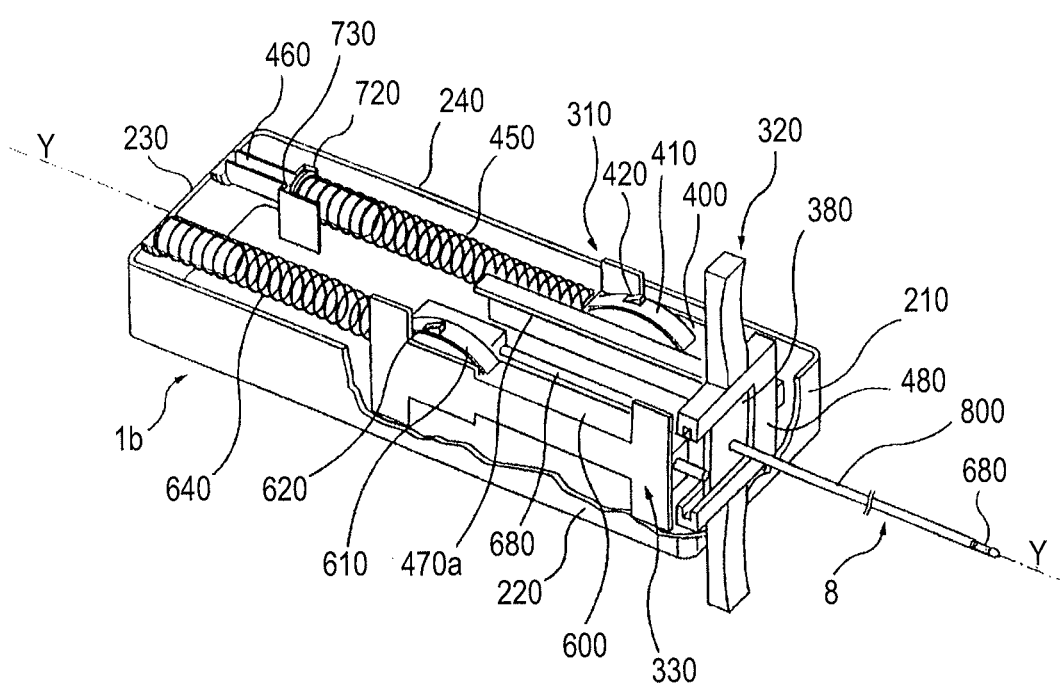
FIG. 7B is a perspective view of the appliance seen in FIG. 7 but without an upper part thereof.
Figures 9, 9A:
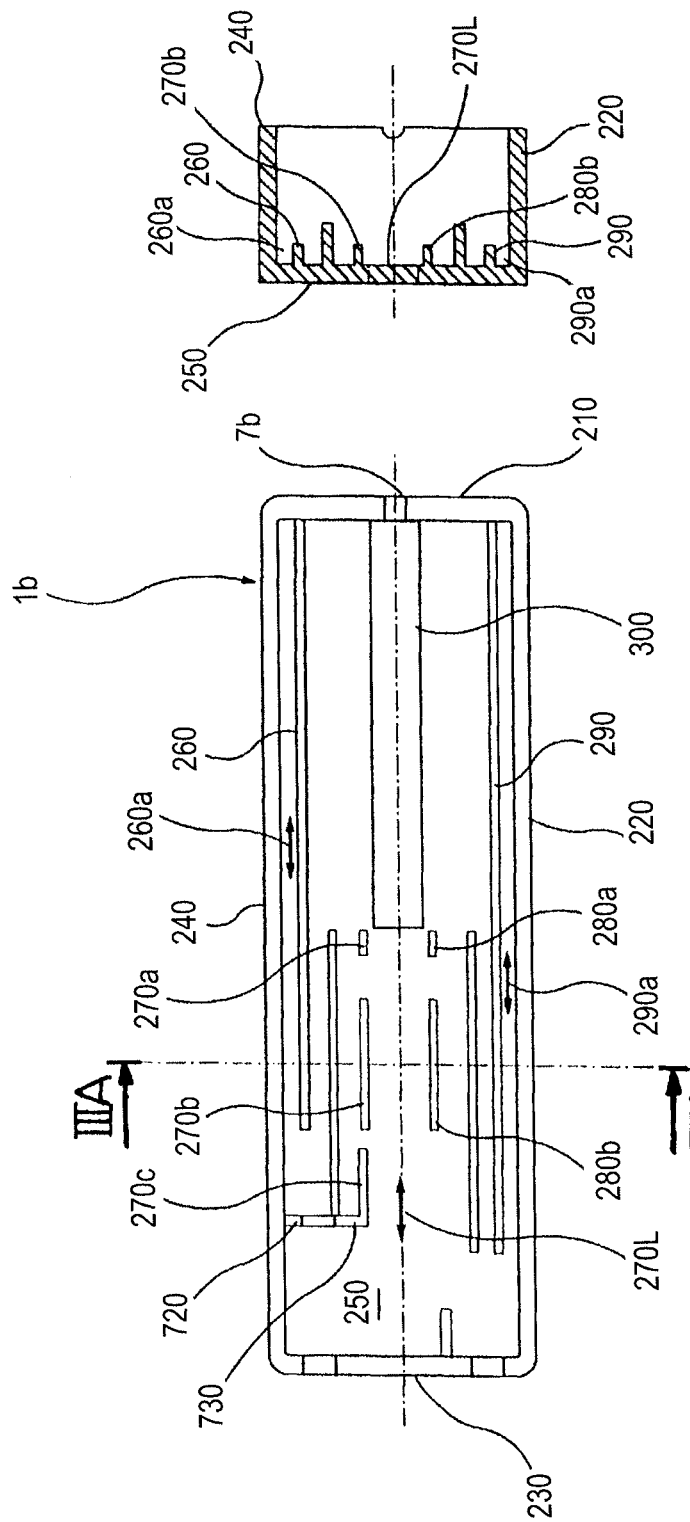
FIG. 9 is a plan view of the appliance shown in FIG. 7.
FIG. 9A is a sectional view along line IIIA-IIIA of FIG. 9.

U.S. Pat. No. 5,951,489 (hereinafter, "the '489 patent"), which is expressly incorporated by reference herein, discloses a handheld biopsy device without vacuum assistance. FIGS. 7-22 illustrate the biopsy device of the '489 patent. With reference to FIGS. 7, 7A and 7B, the illustrative device extends lengthwise along a y-axis and outside it is made up of a case shaped in two semi-shells 1a and 1b.

Upper shell 1a seen in FIGS. 7-8A is made up of a front wall 2, a side wall 3, a back wall 4, a side wall 5 and an upper wall 6, where front wall 2 includes a semi-hole 7a for the passage of a biopsy needle 8. Upper wall 6 includes a slot 9, a first portion 100 bending in a transversal plane and a second portion 110 bending in a longitudinal plane. An inner surface of wall 6 includes a first longitudinal elevation 120 which configures a longitudinal slicing channel 120a with wall 5, a couple of elevations 130 and 140 which configure a central longitudinal sliding channel 130a between them, a second elevation 150 which configures a longitudinal sliding channel 150a with wall 3, a holding tooth 160, a pushing tooth 170, a holding tooth 180, a pushing tooth 190 and a pushing tooth 100a. The pushing teeth 170 and 190 are carried by bending part 110, and the tooth 100a is carried by bending part 100, so as to be mobile downwards if a force is applied inwards on outer bending part 110 or 100.

The lower shell 1b (FIGS. 7-9A) is formed with front wall 210, a side wall 220, a back wall 230, a side wall 240 and a lower wall 250, where front wall 210 presents a semi-hole 7b for the passage of needle 8 mentioned above. The lower wall 25 includes a longitudinal elevation 260 which configures a longitudinal sliding channel 260a with wall 240, a double series 270a, 270b, 270c and 280a, 280b, of elevations aligned lengthwise which configure a central sliding channel 270L between them, an elevation 290 which configures a longitudinal sliding channel 290a with wall 220 and, in the center, a passing slot 300.

Inside the shells 1a and 1b a cannula slider 310, a loader slider 320 and a stylet slider 330 slide lengthwise.

The cannula slider 310, FIGS. 10, 10A and 8A, is formed for its guided longitudinal sliding, with a couple of upper flaps 340 and 350 suitable for sliding in the longitudinal channel 120a of upper shell 1a and, below, a couple of flaps 360 and 370 suitable for sliding in the longitudinal channel 260a of lower shell 1b. The four mentioned flaps 340, 350, 360, 370 are carried by a main body 400 having on its top an elastic bridge 410 equipped with a holding mobile tooth 420 and inside the body 400 a back housing 430 and an additional front housing 440 are provided. Housing 430 receives a spring 450 which has its opposite end triggered on a pin 460 equipped with a longitudinal hole 520. The pin 460 is carried by wall 230 of shell 1b and by two shoulders 720 and 730 seen in FIGS. 13A and 13B. The housing 440 houses a spring 700 and spring guide rod 490 with a diameter which is smaller than that of the hole 520 so as to pass through the interspace between the two housings 430 and 440 for the reasons described and explained hereinafter. A front part of the cannula slider 310 includes a head 380 extending transversely beyond y-axis having coaxially with respect to the latter a hole 390 suitable for carrying cannula 800 of needle 8.

With reference to the loader slider 320 (FIGS. 11 and 11A) it slides lengthwise guided in the upper sliding channel 13a of the shell 1a and in the lower guiding channel 270L of shell 1b. The loader slider 320 is provided with a fork central body with tines 470a and 470b, a head 480, spring guiding rod 490 on which spring 700 is triggered, and a couple of wings 500a and 500b suitable for sliding inside respective slots 9 and 300 of shells 1a and 1b.

Figure 13A:
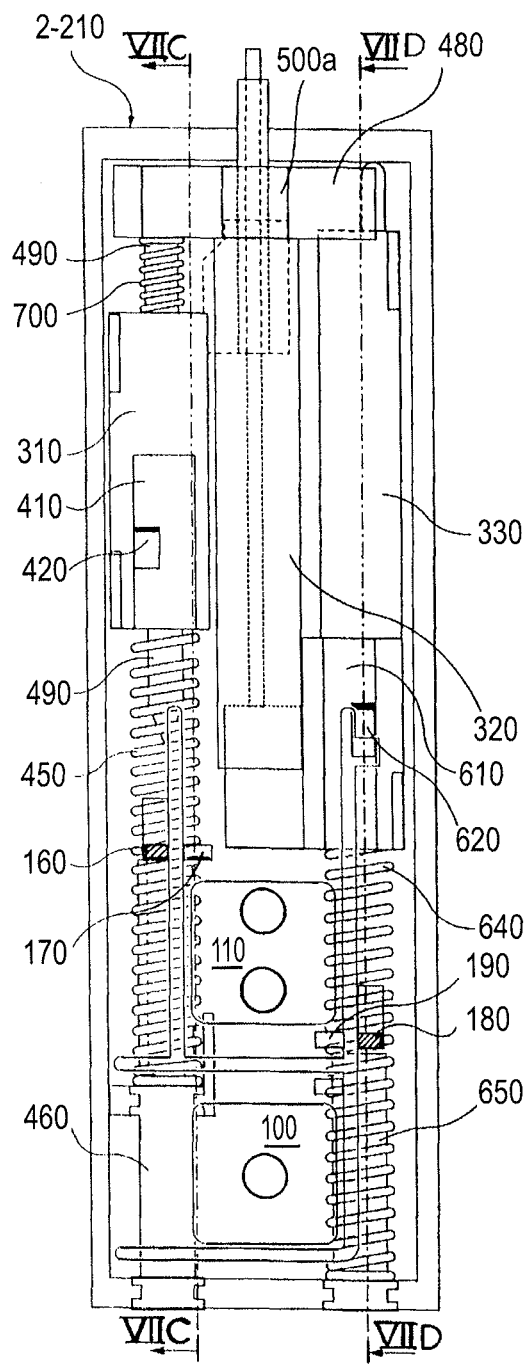
FIG. 13A is a top schematic view in transparency through an upper wall of the appliance shown in FIG. 7 and illustrating the appliance in an idle state of the load cycle.
Figure 13B:
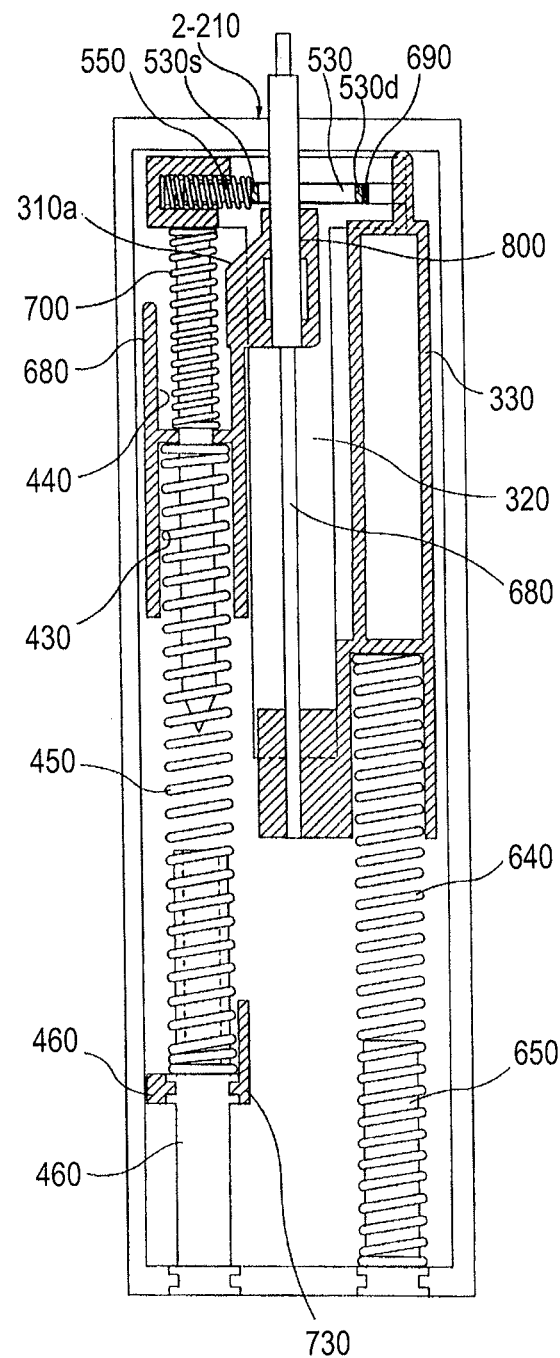
FIG. 13B is a sectional top view along the median horizontal plane of the surgical appliance seen in FIG. 13A.
Figure 13C:
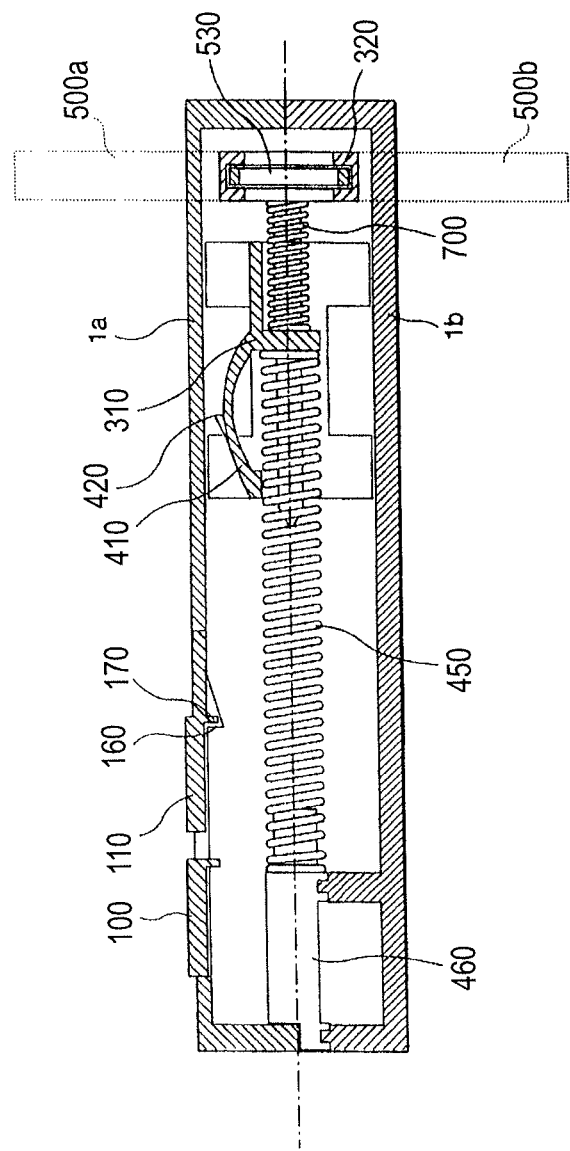
FIG. 13C is a sectional view along line VIIC-VIIC of FIG. 13A.
Figure 13D:
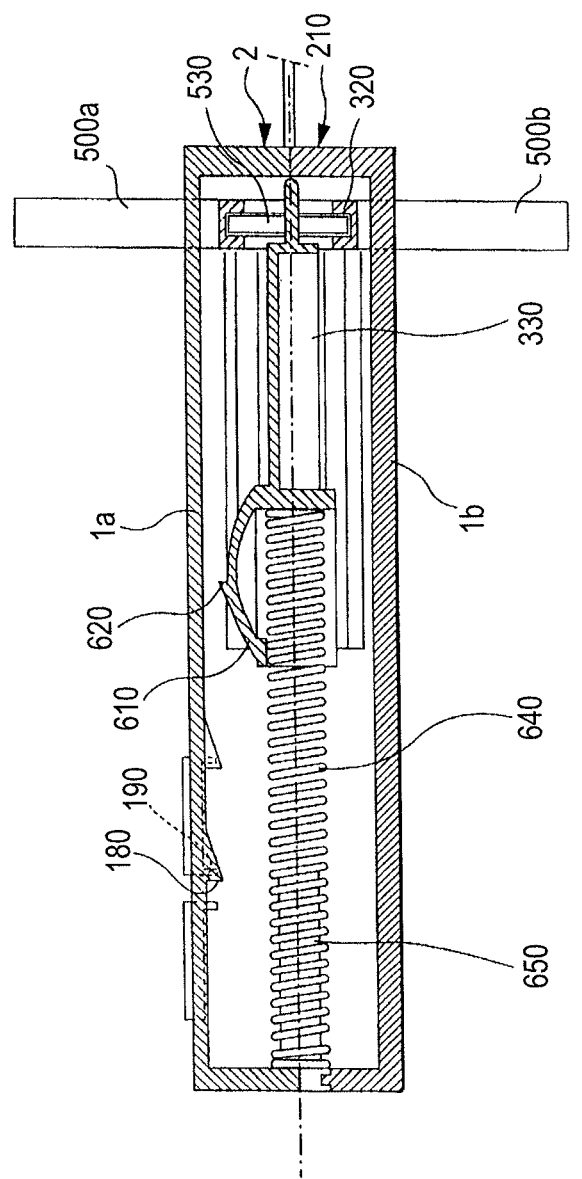
FIG. 13D is a sectional view along line VIIID-VIIID of FIG. 13A.

With reference to head 480, it presents a "U" reversed configuration in which two transversal guides 510a and 510b are made and suitable for carrying a square element 530 sliding transversely and loaded elastically by a spring 550, which as seen in FIG. 13B stops on a limit stop 690 to inhibit its exit. The square 530, when inserted into guides 510*a* and 510*b* has two vertical sides 530*s* and 530*d* mobile transversely and respectively destined to selectively meet front faces of cannula slider 320 and stylet slider 330 as better described hereinafter.

Figure 12:
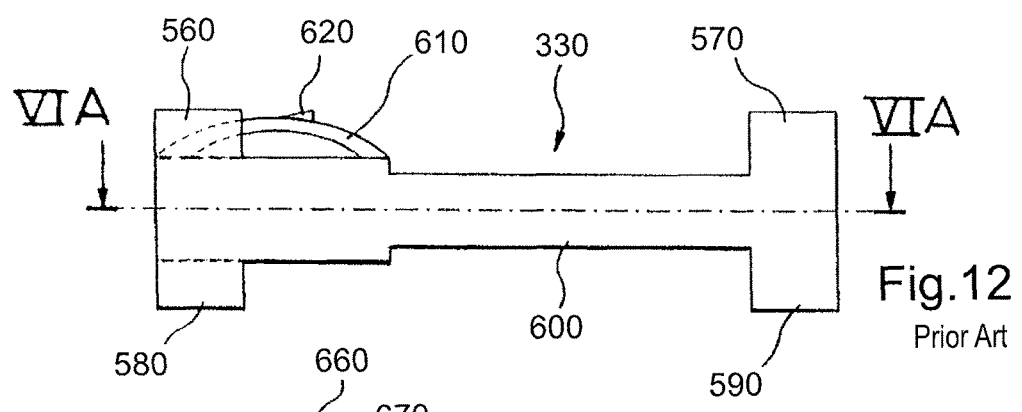
FIG. 12 is a side view of the appliance shown in FIG. 7A.
Figure 12A:
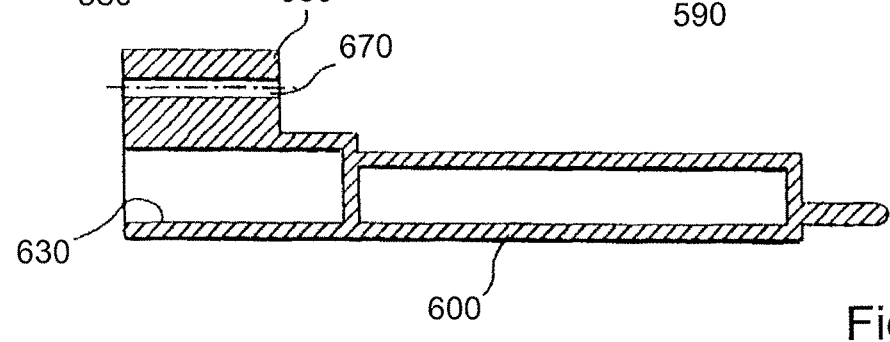
FIG. 12A is a sectional view along lines VIA-VIA of FIG. 12.

The stylet slider 330 (FIGS. 12 and 12A) is formed with a couple of upper flaps 560 and 570 suitable for sliding in the longitudinal channel 150*a* and, below, a couple of flaps 580 and 590 suitable for sliding in the lower longitudinal channel 290*a*. The mentioned flaps are carried by a main body 600 having on its top an elastic bridge 610 equipped with a mobile tooth 620 and a housing 630 inside. The housing 630 carries a spring 640 which has its opposed end triggered on a pin 650 carried by the wall 230 of lower shell 1*b*. The back part of the stylet slider 330 includes a head 660, extending transversely beyond y-axis, which includes a hole 670 that is coaxial with respect to the y-axis in which a stylet back and/or control end 680 of needle 8 is triggered.

With reference to FIGS. 13A, 13B, 13C and 13D, they illustrate the appliance at the beginning of its loading for the subsequent removal, that is in a first idle position.

In the idle position sliders 310, 320 and 330 are pressed on front walls 2 and 210 by the respective springs 450, 700 and 640.

The square 530, sliding transversely to the y-axis, is loaded by spring 550 which presses it on limit stop 690 and, as seen in FIG. 13B, it has two mobile strikers 530*s* and 530*d*, of which striker 530*s* is aligned lengthwise to meet inclined plane 310*a* of element 310 and striker 530*d* is aligned lengthwise to meet element 330 front part.

To obtain appliance loading in view of the removal the operator must wind cannula slider 310 first and then stylet slider 330.

The operator acts to move the loader slider 320 backwards by grasping the two wings 500*a* and 500*b* extending outside shells 1*a* and 1*b*.

Figure 14:
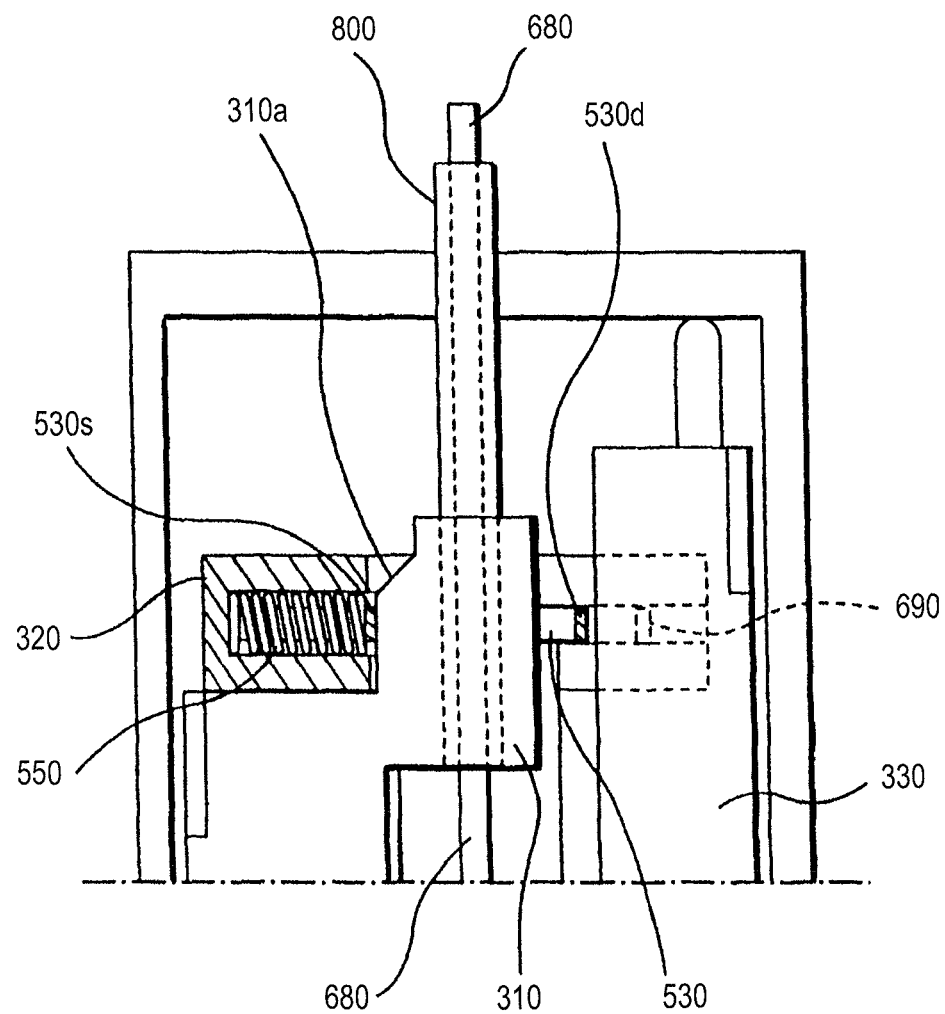
FIG. 14 is a view illustrating an operative detail.

With reference to FIG. 14, which illustrates a special operative arrangement, when the loader slider 320 starts moving towards the appliance back part to begin winding or loading operations, striker 530*s* interferes with inclined plane 310*a* thus entailing a displacement of the relative square 530 on the left, so that striker 530*d* does not interfere with element 330 front part.

Figure 15A:
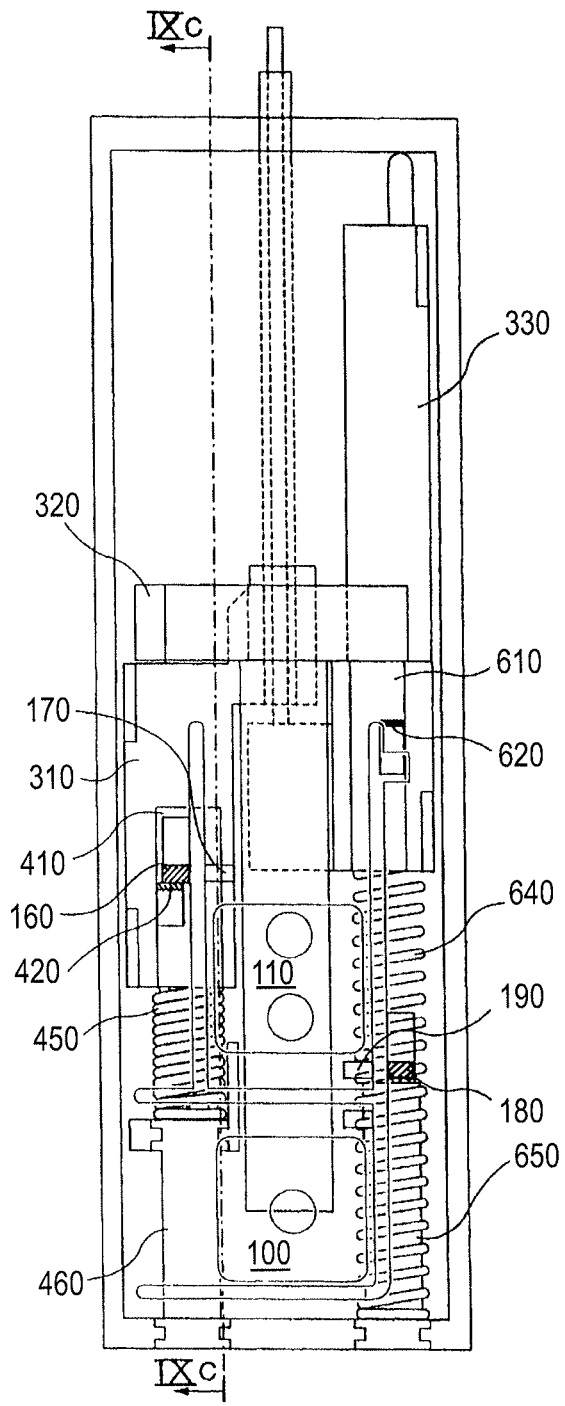
FIG. 15A is a top schematic view in transparency through the upper wall of appliance of FIG. 7 illustrating the appliance in a second position of the load cycle.
Figure 15B:
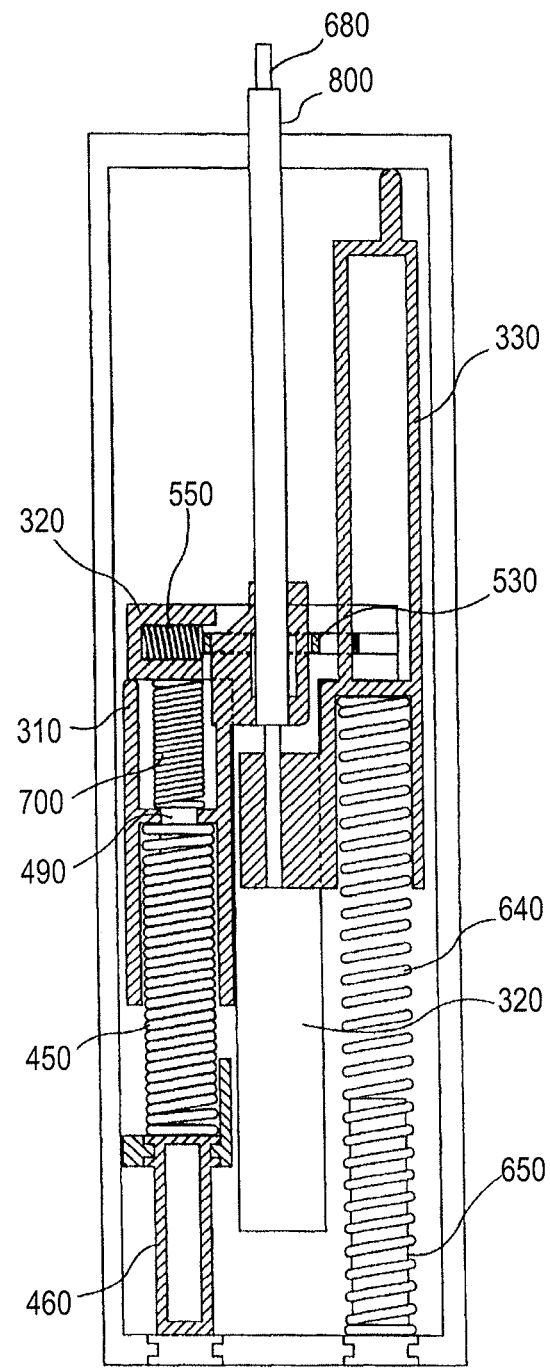
FIG. 15B is a sectional view along the horizontal median plane of surgical appliance in the position shown in FIG. 15A.
Figure 15C:
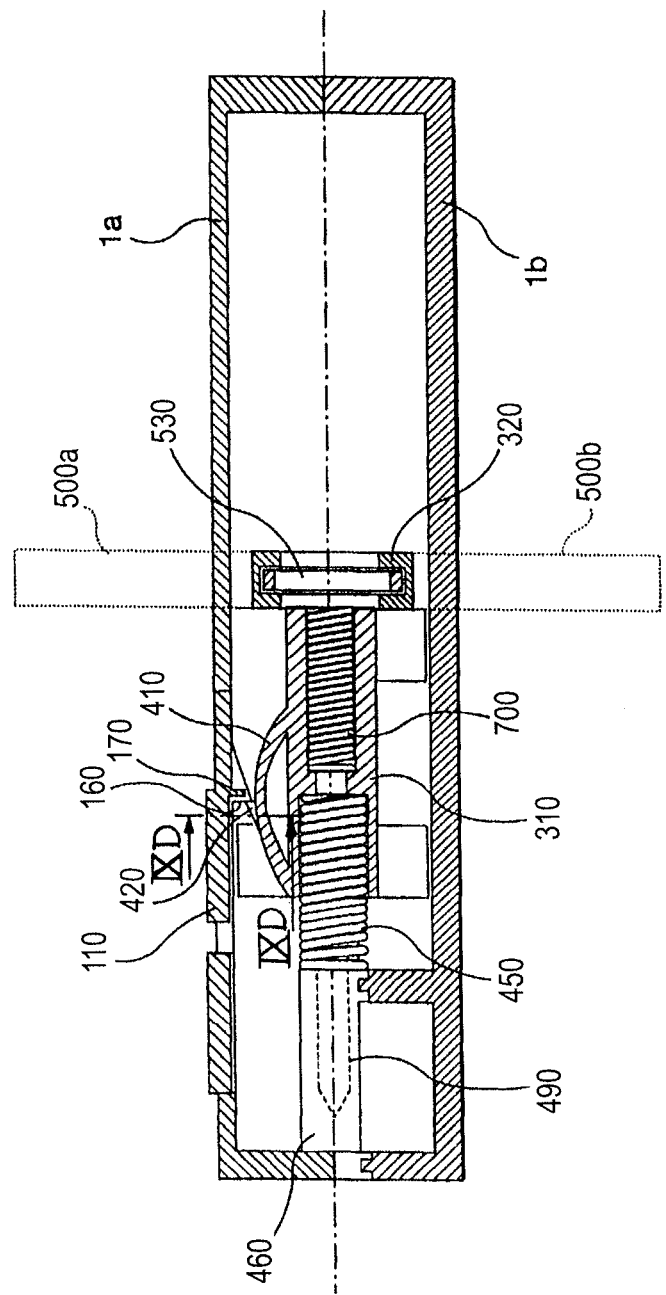
FIG. 15C is a sectional view along line C-C of FIG. 15A.
Figure 15D:
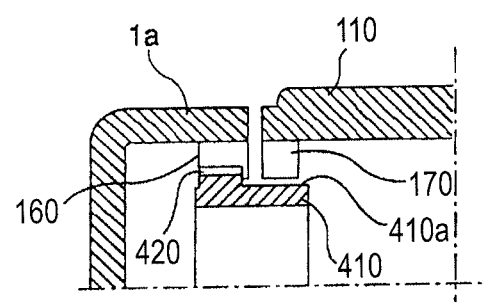
FIG. 15D is a sectional view along line E-E of FIG. 15C.

With reference to FIGS. 15A, 15B and 15C, the loader slider 320 has been pulled backwards and it has dragged cannula slider 310 with itself. The cannula slider, moving backwards, has compressed spring 450 and mobile holding tooth 420, carried by elastic bridge 410, and hooking fixed holding tooth 160 carried by shell 1*a*. With reference to this hooking, see FIGS. 15C and 15D, please note that mobile holding tooth 420 clutches with fixed tooth 160 and that bridge 410 includes an upper portion 410*a*, extending lengthwise and arranged transversely at the tooth side 420, which is aligned vertically with pushing tooth 170 carried by bending part 110, so that, by pressing the bending part 110, pushing tooth 170 presses on bridge 410 and as it is pressed down it is lowered with subsequent release of teeth 160 and 420 for the reasons described hereinafter.

Figure 16A:
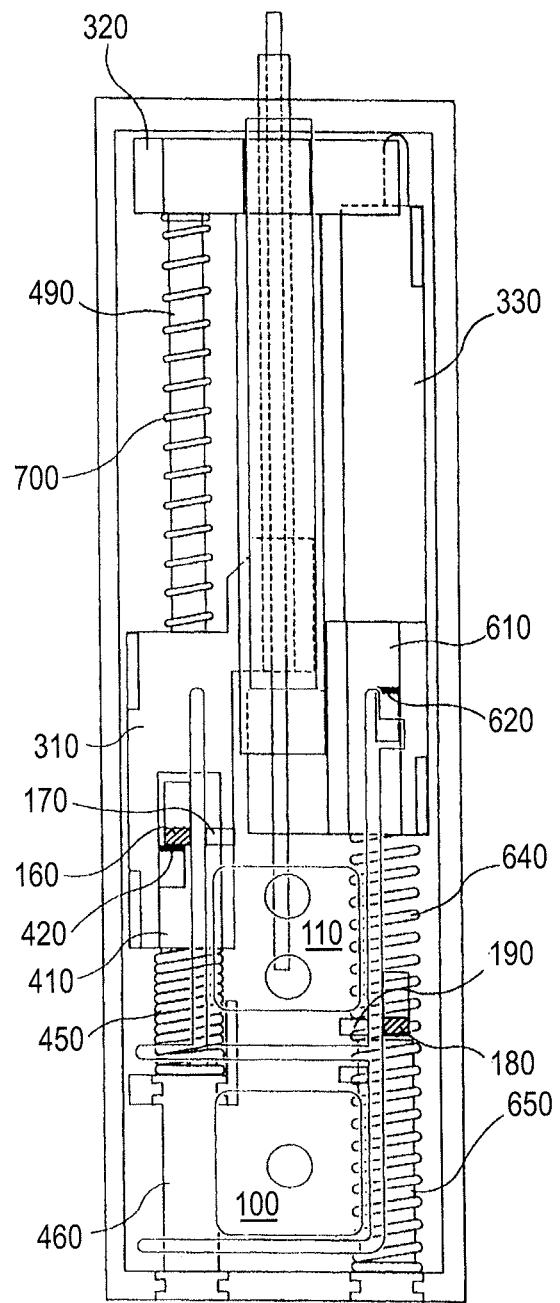
FIG. 16A is a top schematic view in transparency through the upper wall of appliance of FIG. 7 illustrating the appliance in a third position of load cycle.
Figure 16B:
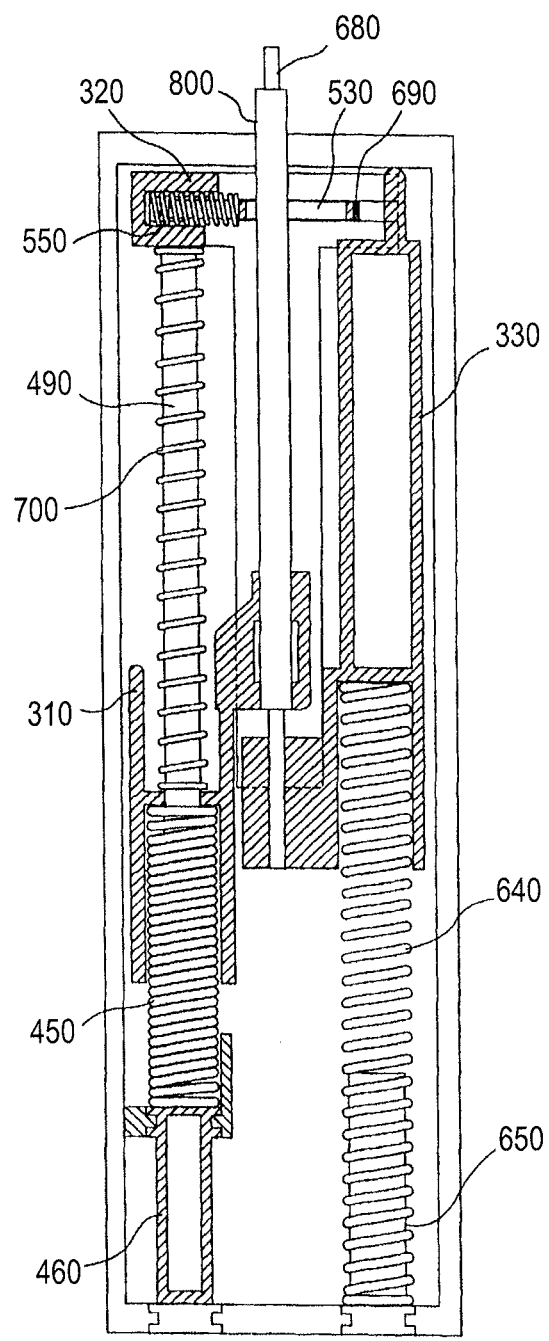
FIG. 16B is a sectional view along median horizontal plane and from surgical appliance top in the position illustrated in FIG. 15A.

With reference to FIGS. 16A and 16B, loader slider 320 after loading cannula slider 310 as mentioned above, returns to the former position by pushing spring 700 while square 530 loaded by spring 550 positions on limit stop 690.

Figure 17A:
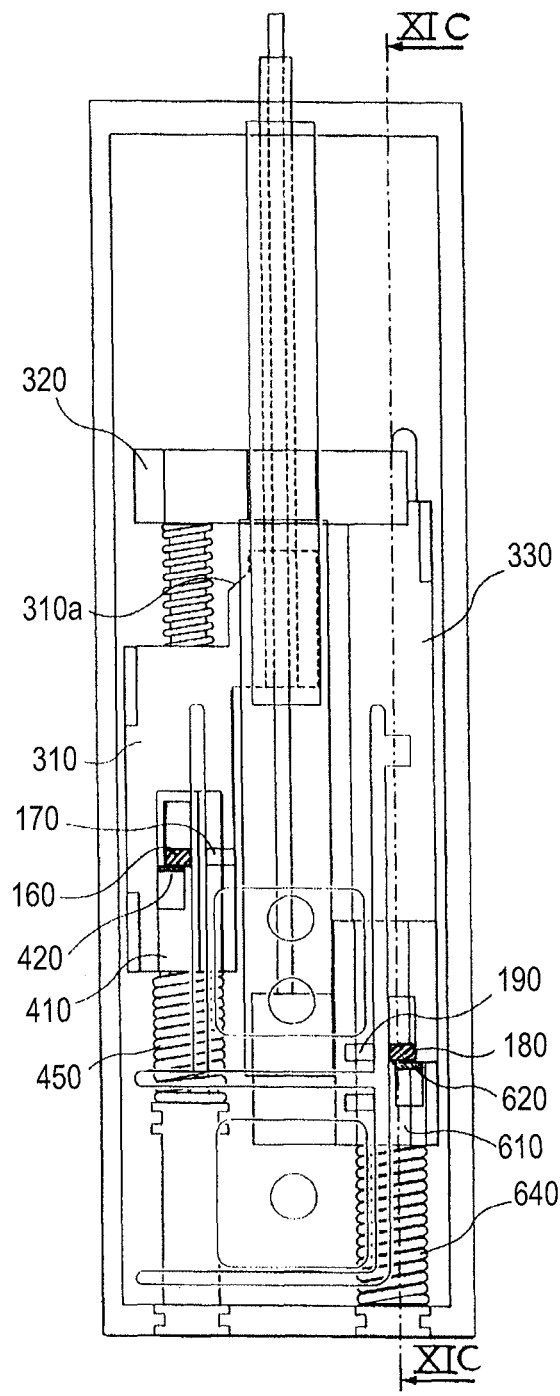
FIG. 17A is a schematic top view in transparency through the upper wall of appliance case of FIG. 7 illustrating the appliance in a third position of the load cycle.
Figure 17B:
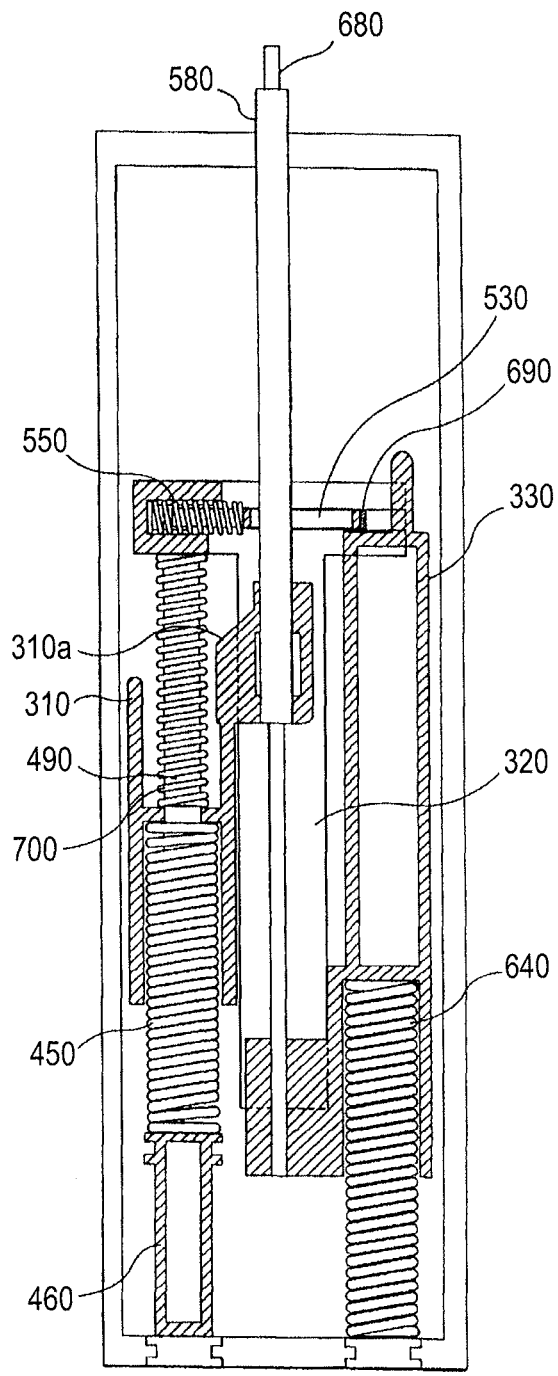
FIG. 17B is a sectional view along median horizontal plane and from the surgical appliance top in the position seen in FIG. 17A.
Figure 17C:
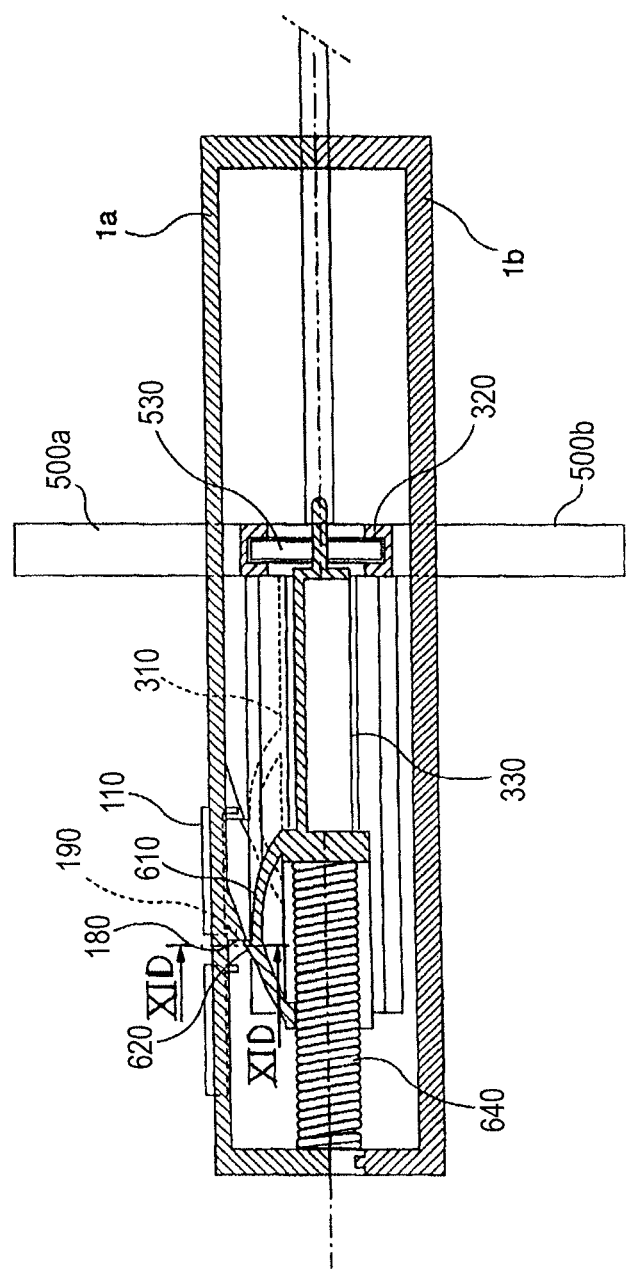
FIG. 17C is a sectional view along line XIC-XIC of FIG. 17A.
Figure 17D:
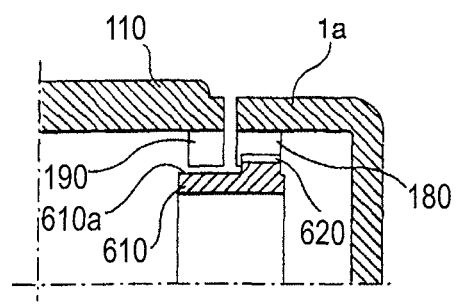
FIG. 17D is a sectional view along line XID-XID of FIG. 17C.

With reference to FIGS. 17A, 17B and 17D, loader slider 320 has been pulled again towards the back and has dragged stylet slider 330 with itself. In this respect please note that since cannula slider 310 is positioned towards the back, square 530 is not subject to transversal displacements by inclined plane 310*a*.

Stylet slider 330, moving backwards, has compressed spring 640 and mobile holding tooth 620, carried by elastic bridge 610, has hooked fixed holding tooth 180 carried by shell 1*a*. With reference to that hooking (FIG. 11D) please note that mobile holding tooth 620 clutches with fixed tooth 180 and that bridge 610 includes an upper portion 610*a*, extending lengthwise and arranged transversely at tooth side 620, which is aligned vertically with pushing tooth 190 carried by bending part 110, so that, by pressing said bending part 110, presses on tooth 190 pushes bridge 610 and as it is pressed down it is lowered with subsequent release of teeth 620 and 180 for the reasons described hereinafter.

Figure 18A:
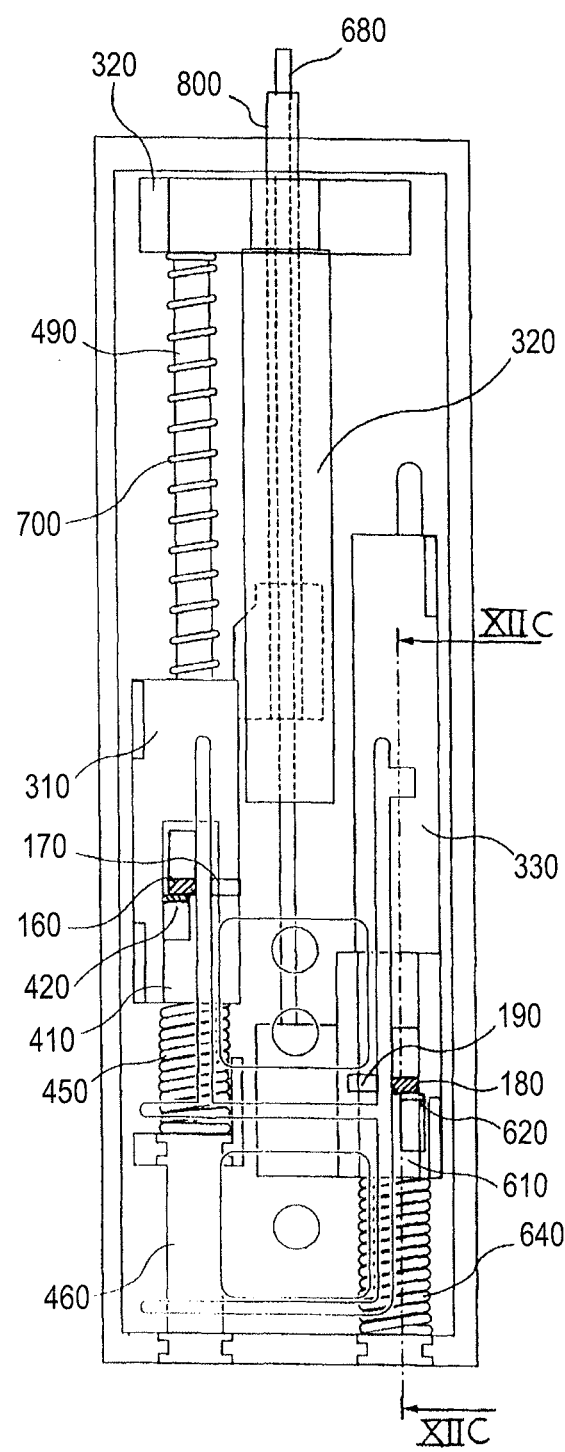
FIG. 18A is a schematic top view in transparency of the upper wall of the appliance case of FIG. 7 illustrating the appliance in a fourth position of load cycle.
Figure 18B:
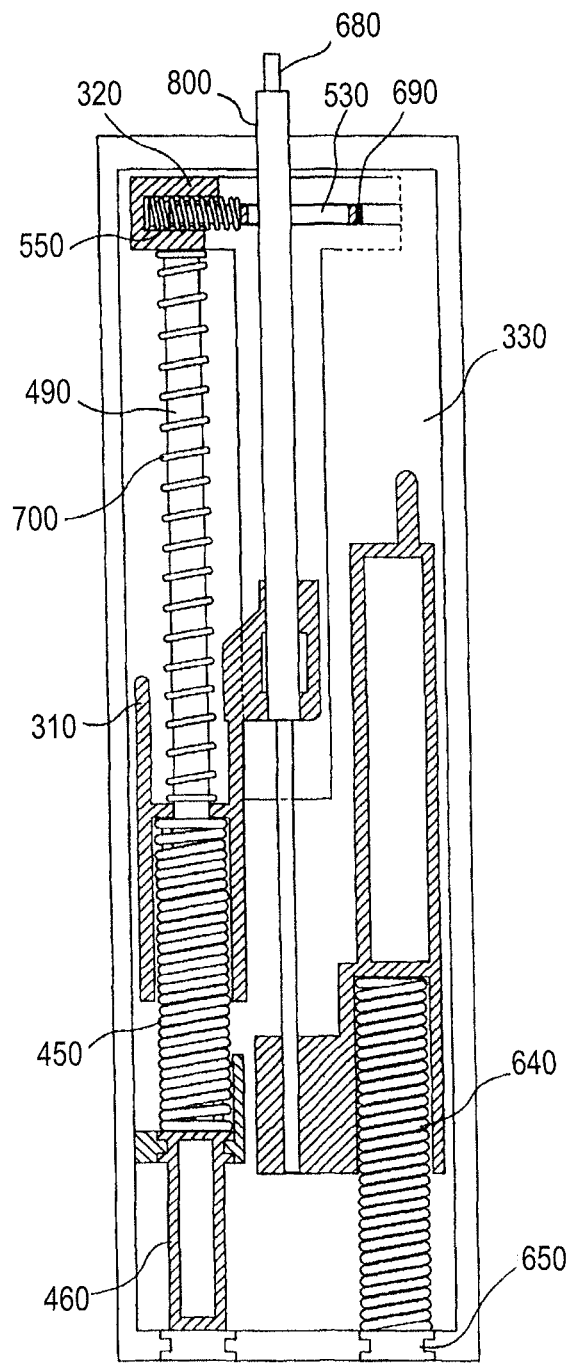
FIG. 18B is a sectional view along horizontal median plane and from surgical appliance top in the position shown in FIG. 18A.
Figure 18C:
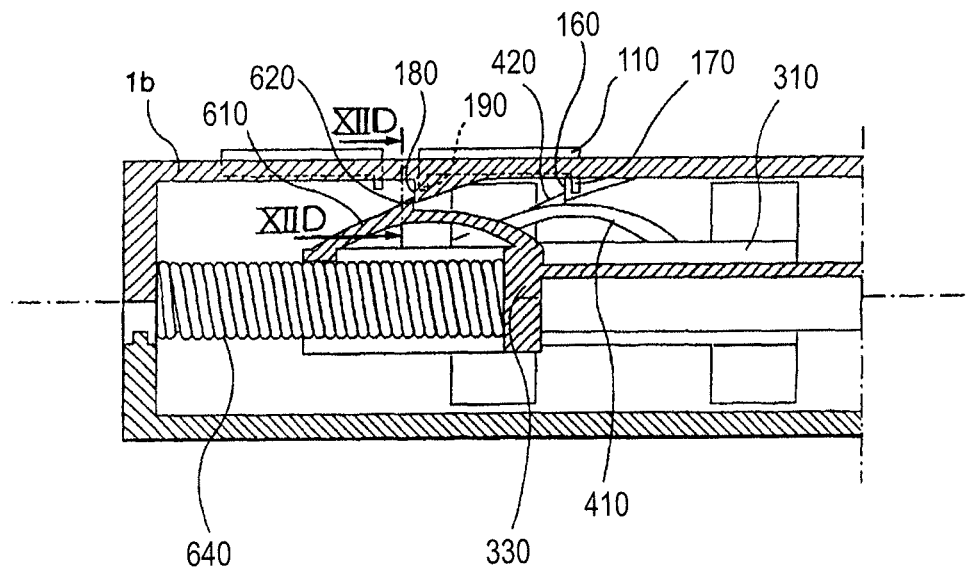
FIG. 18C is a sectional view along plane XIIC-XIIC of FIG. 18A.
Figure 18D:
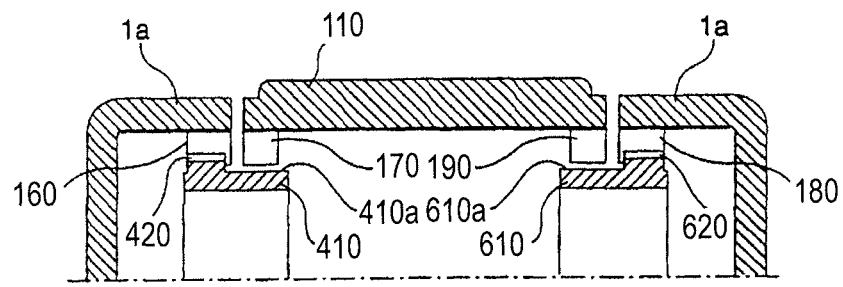
FIG. 18D is a sectional view along line XIID-XIID of FIG. 18C.

With reference to FIGS. 18A and 18B, loader slider 320 after loading stylet slider 330 as mentioned above, returns to its former position by pushing spring 700.

After executing the above-mentioned winding operations (FIGS. 18C and 18D) the stylet slider 330 is wound and held in position through hooking of teeth 180-620 while cannula slider 310 is wound and held in position through hooking 420-160. Furthermore, bending part 110 has two pushing teeth 190 and 170 where pushing tooth 190 can press elastic bridge 610 of cannula slider 330 in order to release it and pushing tooth 170 can press elastic bridge 410 of stylet slider 310 to release it.

With reference to the type of removal to be performed, the operator must wind the appliance as described above first and then insert needle 8 in the tissue and position its free point in the area destined to removal.

At this point the operator may opt for two different types of removal, a first type where the stylet 680 and the cannula 800 are advanced in successive quick sequence by a single control, or a second type of removal where stylet 68 is advanced by a first control and cannula 800 by a second control.

With reference to first type of removal (FIGS. 19 and 20) the operator, applying a strength directed from outside to inside on bending element 110, moves pushing teeth 190 and 170 downwards with different movements, where tooth 190 during bending phase executes downwards movements which are greater with respect to tooth 170.

Figure 19:
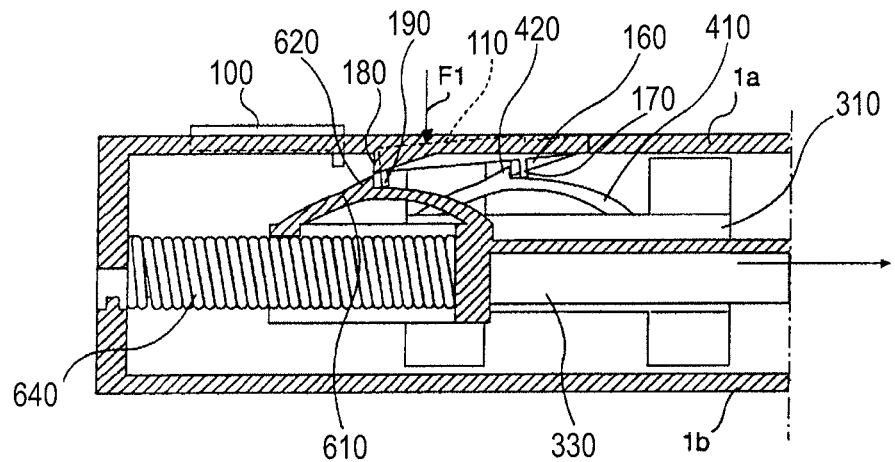
FIGS. 19 and 20 are two schematic longitudinal sectional views illustrating a first and second operative phases in the execution of a first type removal aiming at advancing stylet and cannula in quick sequence.
Figure 20:
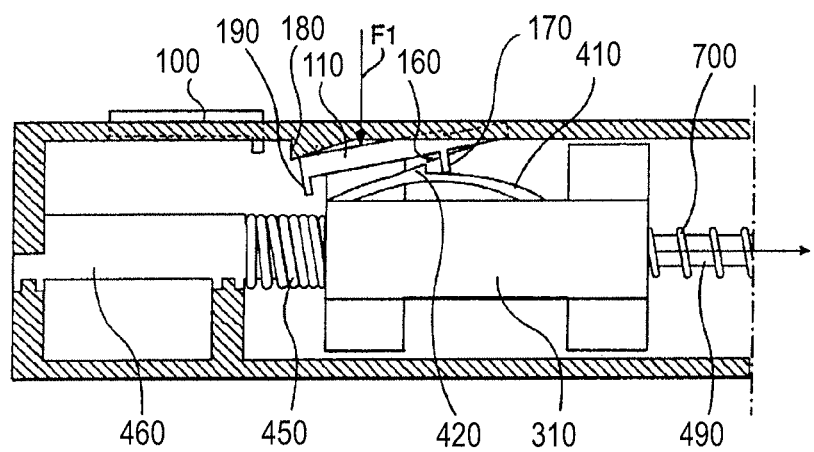

More particularly, flexure of bending element 110 entails first stylet slider 330 release through pushing tooth 190 pressure on bridge 610 which involves mobile holding tooth 620 to be released from fixed holding tooth 180 with subsequent advancement of stylet slider 330 by pre-wound spring 640 (FIG. 19). Then, due to further flexure of bending element 110, it entails mobile holding tooth 420 to be released from fixed holding tooth 160 with subsequent advancement of cannula slider 31 by pre-wound spring 450 as shown in FIG. 20.

In such a manner advancement of stylet 680 and cannula 800 is obtained in quick sequence as required for first type of removal, and in case stylet 680 and therefore the relative slider 330 because of a particularly hard tissue do not reach advancement limit stop, cannula 800 executes its cutting stroke all the same since the release of the holding means 420-160 is independent from the system relative to stylet slider 330.

Figure 21:
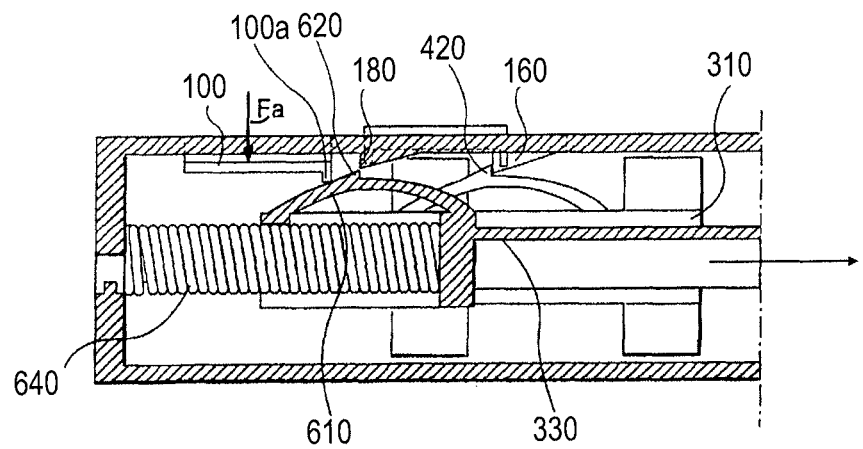
FIGS. 21 and 22 are two sectional longitudinal schematic views illustrating a first operative phase and a second operative phase in the execution of a removal of the type aiming at advancing the stylet by a first control and the cannula by a second control.
Figure 22:
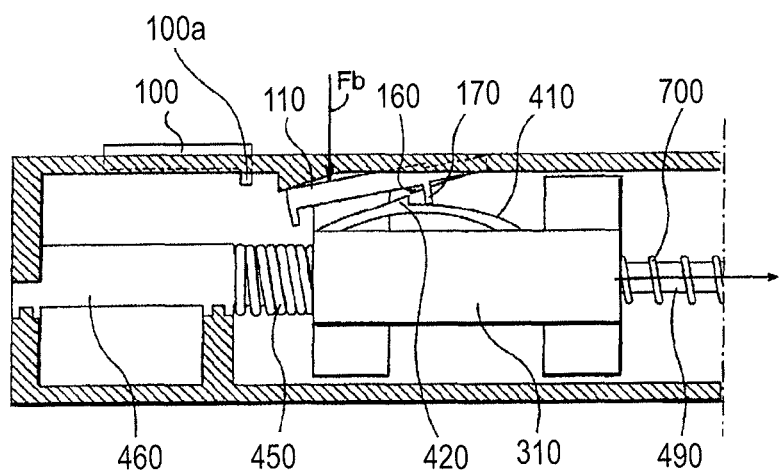

With reference to second type of removal (FIGS. 21 and 22) the operator, applying a first control through a first strength FA directed from outside to inside on the bending element 100, moves bridge 610 downwards through pushing tooth 10*a*, thus entailing the release of holding tooth 620 from holding tooth 180 with subsequent advancement of stylet slider 330 by pre-wound spring 640, see FIG. 21. Then, after examining the correct arrangement of needle point 8 by magnetic resonance, computed axial tomography or other systems, the second control is operated through the application of a strength FB on bending element 110 by releasing cannula slider 310 as aforementioned.

In such a manner advancement of cannula 800 is obtained also in case slider 330, because of a particularly hard tissue found stylet point 680, does not reach advancement limit stop, since the release of the holding means 420-160 of cannula slider 310 are not associated with stylet slider 330.

Vacuum Assisted Handheld Biopsy Device

As noted above, the inventive handheld biopsy device may include the above-described handheld biopsy devices as the primary operative structure. For clarity, only the modifications are discussed in detail herein.

Figure 23:
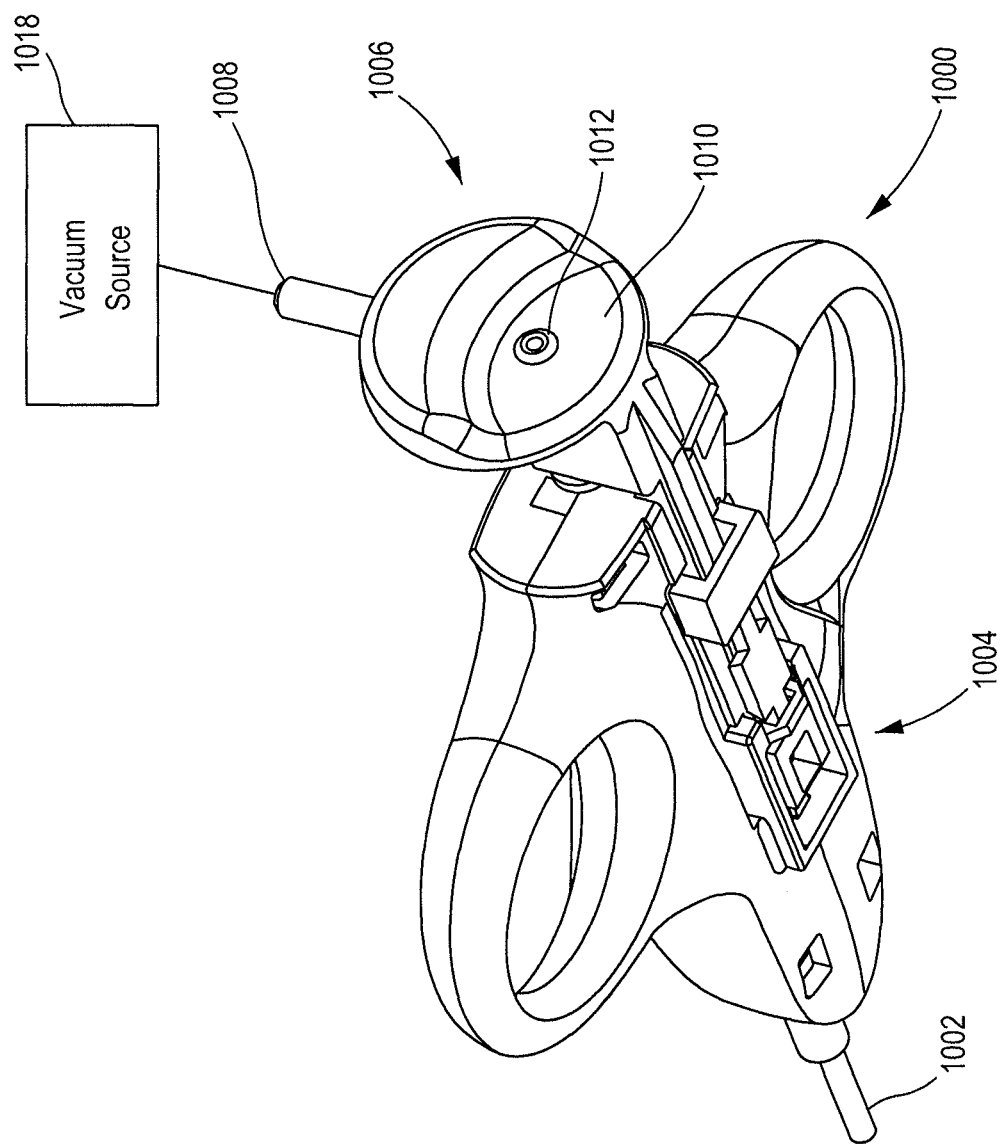
FIG. 23 is a perspective view, with omissions, of a vacuum assisted handheld biopsy device in accordance with aspects of the present invention.
Figure 24:
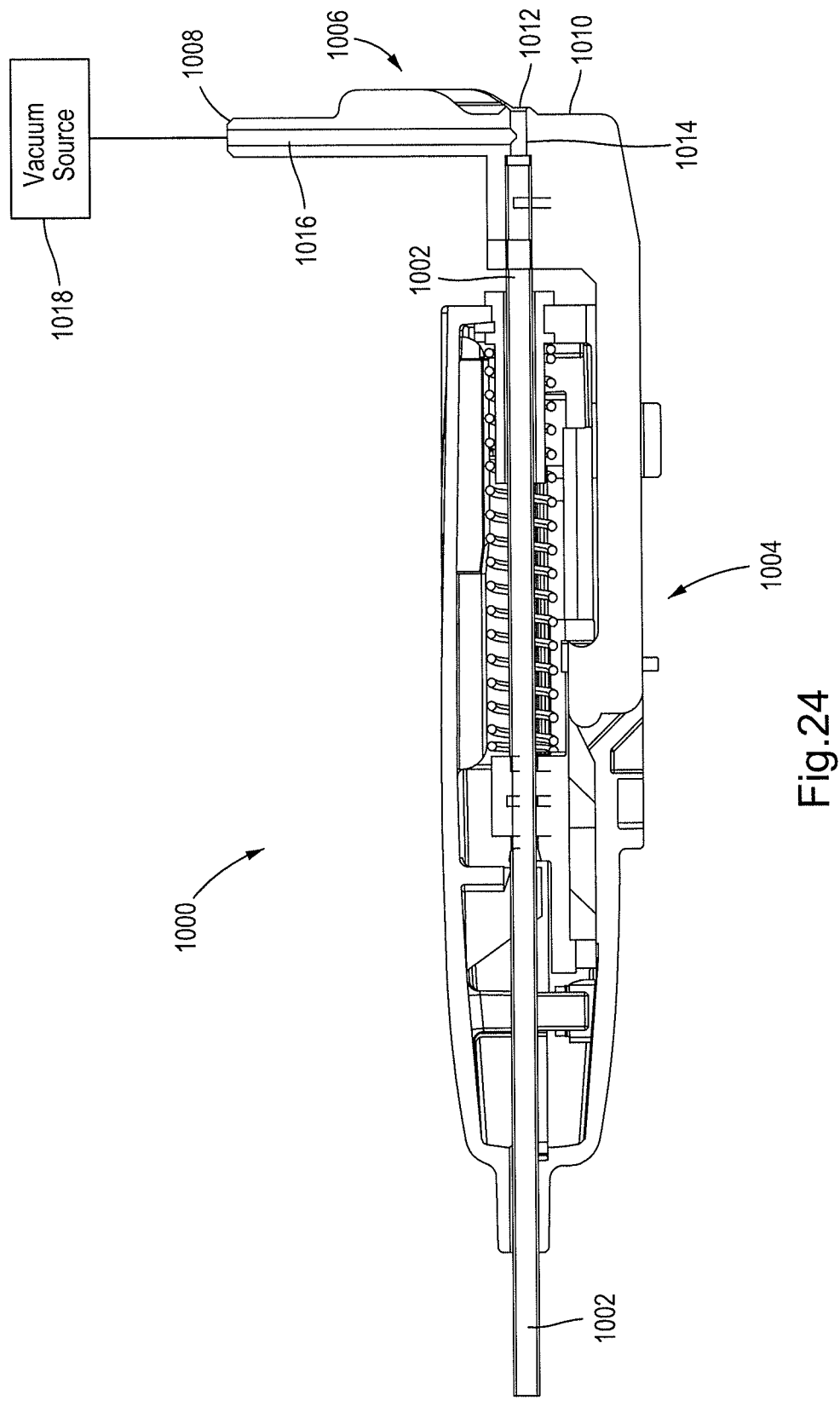
FIG. 24 is a side cross-sectional view of the vacuum assisted handheld biopsy device of FIG. 23.

FIGS. 23 and 24 show the housing portion of a vacuum assisted handheld biopsy device 1000. The aspects shown in FIGS. 23 and 24 correspond to the prior art device shown in FIGS. 1-6 above. FIG. 23 shows a perspective view, with omissions, of the vacuum assisted handheld biopsy device 1000, in accordance with aspects of the present invention. The vacuum assisted handheld biopsy device 1000 generally includes a stylet 3000, 4000, 5000, 6000 (see FIGS. 27A-30E), of which only the rear portion tube 1002 of the stylet is shown. The stylet tube 1002 passes through a housing 1004. The device includes an actuator 1006 slideably coupled with the housing, and a vacuum tube 1008. The stylet 3000, 4000, 5000, 6000 (see FIGS. 27A-30E) is slideably coupled with a cannula (not shown). The operation and relative movement of the stylet and cannula is the same as in the prior art device discussed above. The actuator 1006 may include a depression 1010 and an opening 1012 passing through the depression 1010. In an aspect of the invention the depression 1010 is shaped to match the contours of an operator's thumb.

FIG. 24 shows a side cross-sectional view of the vacuum assisted handheld biopsy device 1000. FIG. 24 shows several of the differences between the vacuum assisted handheld biopsy device 1000 as compared to the prior art device of FIGS. 1-6. As shown in FIG. 24, the stylet tube 1002 extends from the end of the device where the tissue sample is taken all the way to the actuator 1006, which is similar to the prior art device. The biopsy device 1000 may further include an ambient air port 1014 extending through the actuator 1006. The ambient air port 1014 terminates with an opening 1012, which allows the stylet tube 1002 and a vacuum source 1018 to be in communication with ambient air. The opening 1012 may be positioned in a depression 1010 portion of the actuator 1006.

As shown in FIG. 24, the vacuum tube 1008 may include a passageway 1016 that communicates with the ambient air port 1014. The vacuum tube 1008 is coupled with a coupling means (not shown) such as flexible tube, for attaching the vacuum tube 1008 to a vacuum source 1018. When the opening 1012 is open, the passageway 1016 is also in communication with ambient air via the ambient air port 1014. When the stylet is in the patient, the path of least resistance for vacuum flow is through port 1012. This is because more force is necessary to extract human tissue as compared to ambient air. Thus, when the opening 1012 is open, a vacuum will not be created in the stylet, even when the vacuum source is turned on. However, when the opening 1012 is closed, the communication of the passageway 1016 and ambient air is severed. Thus, with less resistant flow path removed, the vacuum source 1018 is directed only to stylet, and will provide a vacuum in the stylet, via communication with the stylet tube 1002. Operation of the device and the stylet structure allowing for the vacuum is discussed in more detail below.

Figure 25:
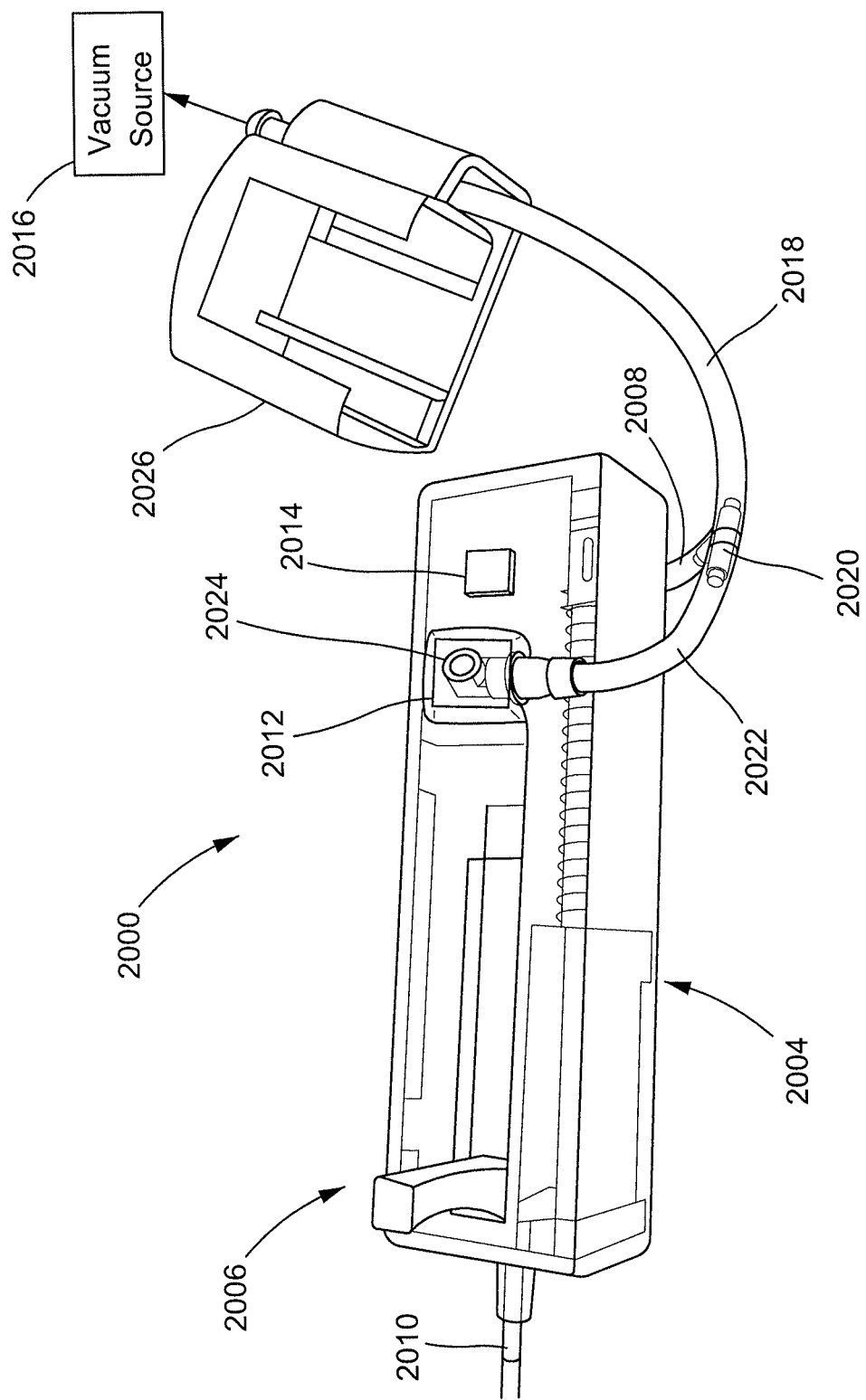
FIG. 25 is a perspective view of a vacuum assisted handheld biopsy device in accordance with additional aspects of the present invention.
Figure 26:
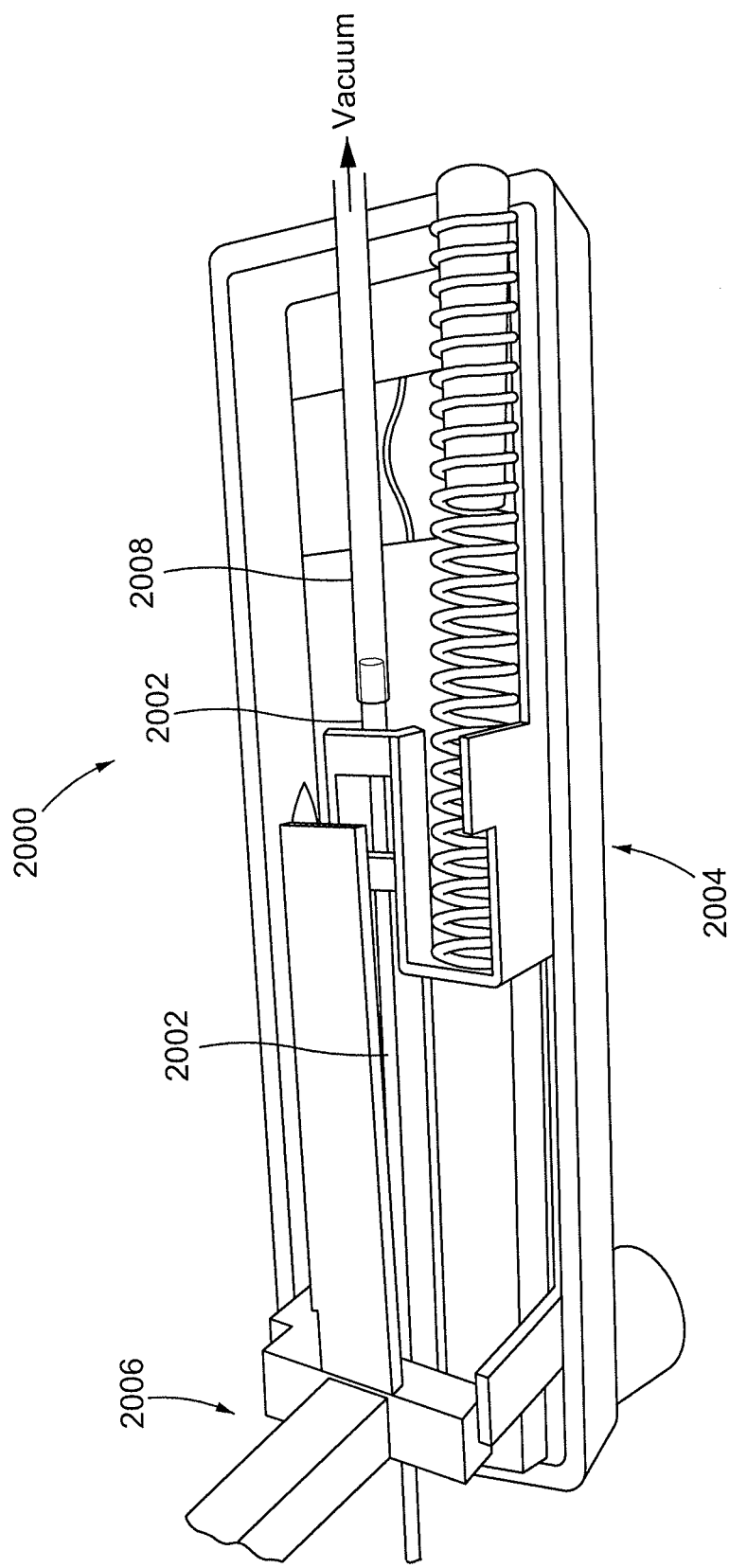
FIG. 26 is a partial perspective view of the internal elements of the vacuum assisted handheld biopsy device of FIG. 25.

FIG. 25 is a perspective view of a vacuum assisted handheld biopsy device 2000 in accordance with additional aspects of the present invention. FIG. 26 is a partial perspective view of the internal elements of the vacuum assisted handheld biopsy device 2000 of FIG. 25. The aspects shown in FIGS. 25 and 26 correspond to the prior art device shown in FIGS. 7-22 and described above.

As seen in FIG. 25, the vacuum assisted handheld biopsy device 2000 generally includes a housing 2004, a cannula 2010, a stylet 3000, 4000, 5000, 6000 (see FIGS. 27A-30E), and an actuator 2006. The stylet may include a stylet tube 2002 passing through a housing 2004. The actuator 2006 is slideably coupled with the housing. The stylet 3000, 4000, 5000, 6000 (see FIGS. 27A-30E) is slideably coupled with a cannula 2010 (FIG. 25). The operation and relative movement of the stylet and cannula is the same as in the prior art discussed above. As with the prior art device, the vacuum assisted handheld biopsy device 2000 may further include a first pushbutton 2012 and second pushbutton 2014, where the first pushbutton 2012 is pressed to take a tissue sample. The first and second pushbuttons 2012, 2014 serve the same functions and operate the same as discussed above with respect to the prior art.

The vacuum assisted handheld biopsy device 2000 may further include a vacuum source 2016 operatively connected with both the first pushbutton 2012 and the rear stylet tube 2002. As shown in FIG. 25, the vacuum source 2016 is connected to the housing 2004 via a first tube 2018. The tube 2018 is split via a connecting branch 2020. The connecting branch 2020 splits the vacuum into two tube paths, a stylet vacuum tube 2008 and a pushbutton vacuum tube 2022. FIG. 26 best shows the connection of the stylet tube 2002 with the stylet vacuum tube 2008. Returning to FIG. 25, the connection between the first pushbutton 2012 and the pushbutton vacuum tube 2022 may include an ambient air opening 2024. The device 2000 may further include a tube securer 2026 to prevent the tubes 2008, 2018, 2022 from interfere with procedure during actuation of the device 2000. More particularly, the tube securer 2026 retains the tubes with the securer such that the operator doesn't feel that tube motion during operation of the device.

Similar to the device 1000, when the opening 2024 is open, the vacuum 2016 is in communication with ambient air. Thus, for the same reasons discussed above, when the opening 2024 is open, a vacuum will not be created in the stylet, even when the vacuum source is turned on. However, when the opening 2024 is closed, the communication of the vacuum 2016 with ambient air is severed. Thus, when the opening 2024 is closed the vacuum is forced to only operate on the stylet vacuum tube 2008, and a vacuum is created in the stylet. Operation of the device and the stylet structure allowing for the vacuum is discussed in more detail below.

As best seen in FIG. 4, in the prior art biopsy devices, the stylet 44 is a uniformly solid cylinder that matches the shape of the hollow portion of the cannula 12. Because of the shape of the stylet in the prior art devices, there is no air path to create a vacuum to the stylet. FIGS. 27A to 30E show stylets in accordance with aspects of the present invention that are used in conjunction with the vacuum to allow the vacuum to reach the stylet, without sucking collected tissue into the stylet tube.

Figure 27D:
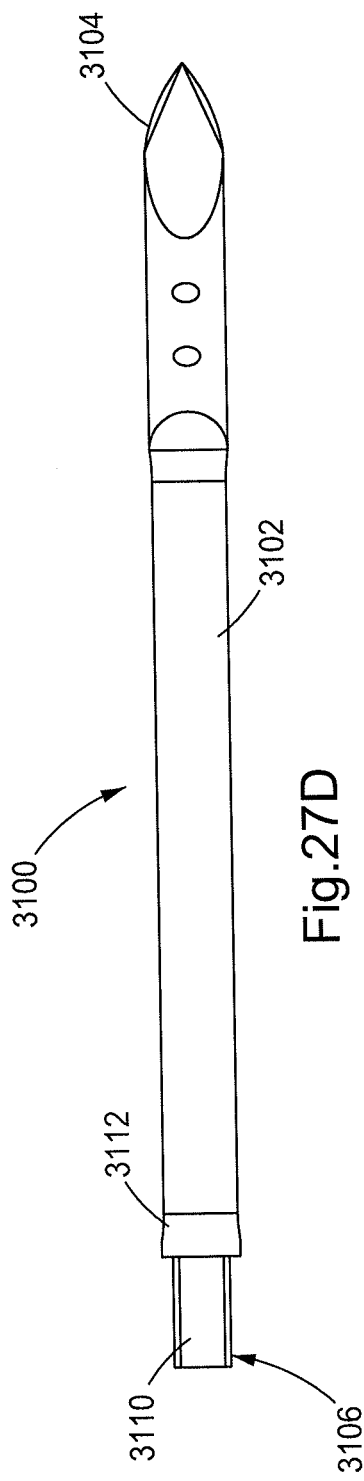
FIG. 27D is a is a top view of the tissue collection portion of the stylet of FIG. 27A.
Figure 27E:
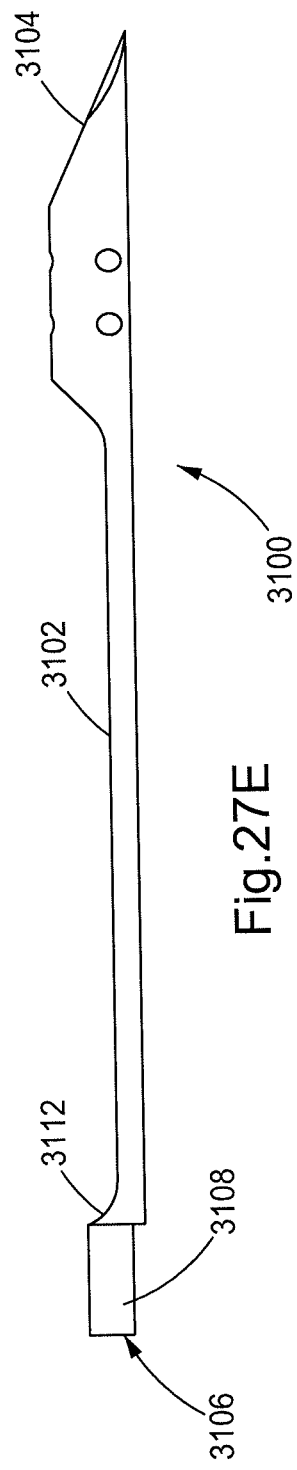
FIG. 27E is a side view of the tissue collection portion of the stylet of FIG. 27A.

FIG. 27A to 27E show a stylet 3000 in accordance with an aspect of the present invention. FIG. 27A shows a perspective view of the stylet 3000. As shown in FIG. 27A, the stylet 3000 may include two portions, a tissue collection portion 3100 and a hollow stylet tube 1002, 2002. When used in the device 1000, the hollow tube extends all the way to the rear of the device 1000, and is coupled with the actuator 1006, as show in FIG. 24. Similarly, when used in the device 2000, the hollow tube extends toward the rear of the device 2000 and is operatively coupled with the actuator 2006, as shown in FIG. 26. Operation of the actuator and movement of the stylet, among other operational features, is described above with respect to the prior art. FIG. 27B shows a side view of the stylet 3000, with the tissue collection portion 3100 inserted into the hollow tube 1002, 2002. FIGS. 27C to 27E show perspective, top, and side views, respectively, of the tissue collection portion 3100 separate from the hollow tube. The tissue collection portion 3100 may include a relatively flat elongated reduced thickness portion 3102 that collects the tissue. The reduced thickness portion 3102 serves the same function as in the prior art devices. The tissue collection portion 3100 may include a sharp tip 3104, also serving the same function as in the prior art. The stylet 3000 (and stylets 4000, 5000, 6000) may be made of any known material suitable in surgical devices and having appropriate strength and other properties for use in a biopsy device, such as stainless steel.

The stylet 3000 may further include an insertion member 3106 located at the rear end of the tissue collection portion 3100. The insertion member 3106 is inserted into the hollow tube 1002, 2002 of the stylet 3000. As best seen in FIG. 27C, the insertion member 3106 may include substantially curved portion 3108 and a substantially flat top portion 3110, thus forming a "D" shaped cross section. The curved portion 3108 is curved to match the inside curve of the hollow tube 1002, 2002. The insertion member 3106 is thus inserted into the hollow tube 1002, 2002 and may be bonded inside of the hollow tube 1002, 2002 via the curved portion 3108, as shown in FIG. 27B. The bonding may be performed by suitable means known in the art, such as via an adhesive, welding, soldering, and the like. Because the flat top portion 3110 does not contact the inner surface of the hollow tube 1002, 2002 of the stylet 3000, an air flow path is provided. As best seen in FIGS. 27C and 27E, the flat portion 3110 extends to a curved ramp 3112, providing a continuous flow path from the hollow tube 1002, 2002 of the stylet. Furthermore, as seen in FIG. 27A, the ramp 3112 has a height smaller than the inside diameter of the stylet tube 1002, 2002, thereby providing the flow path. It has been found that when the above-described features are included in the stylet 3000, the structure focuses the vacuum and avoids sucking tissue into the hollow tube 1002, 2002.

Figure 28C:
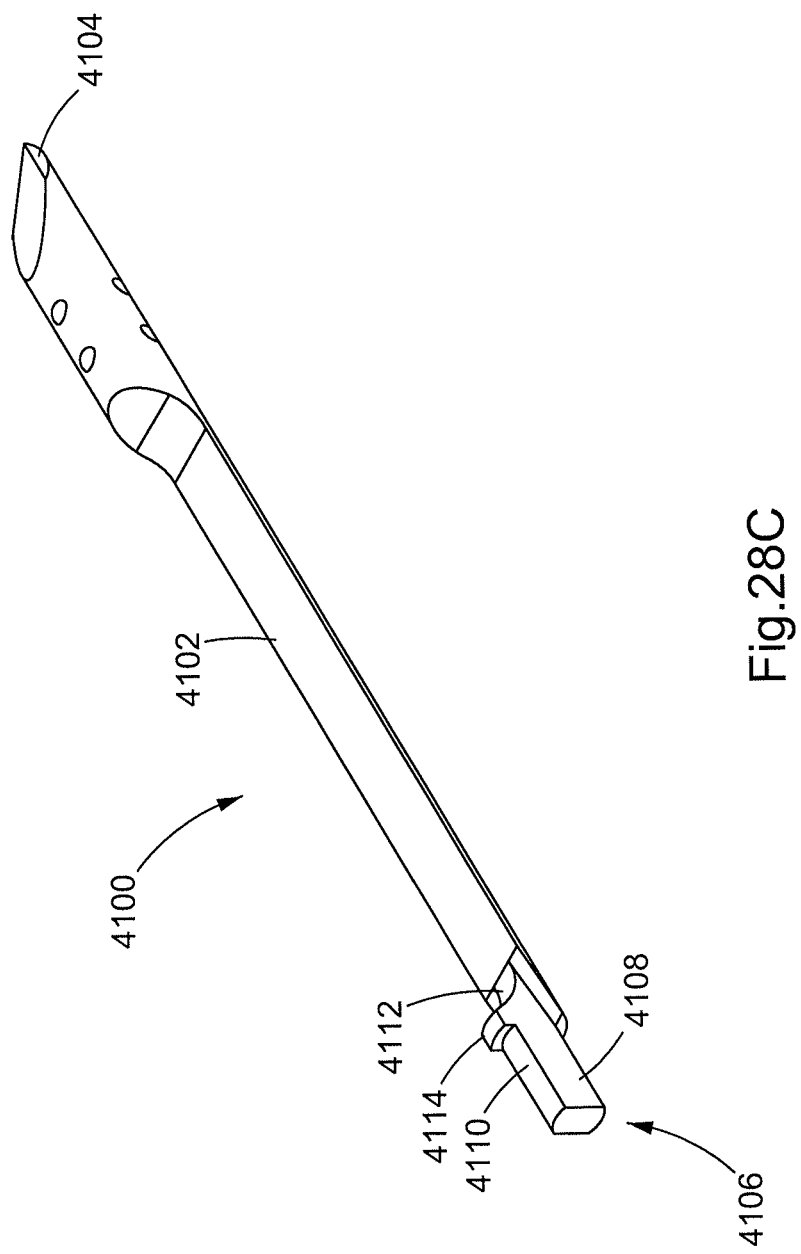
FIG. 28C is a perspective view of the tissue collection portion of the stylet of FIG. 28A.
Figure 28D:
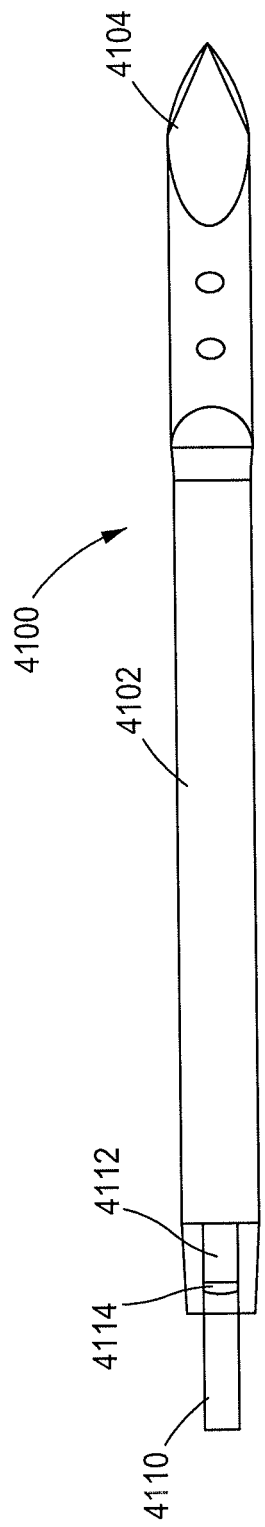
FIG. 28D is a is a top view of the tissue collection portion of the stylet of FIG. 27A.
Figure 28E:
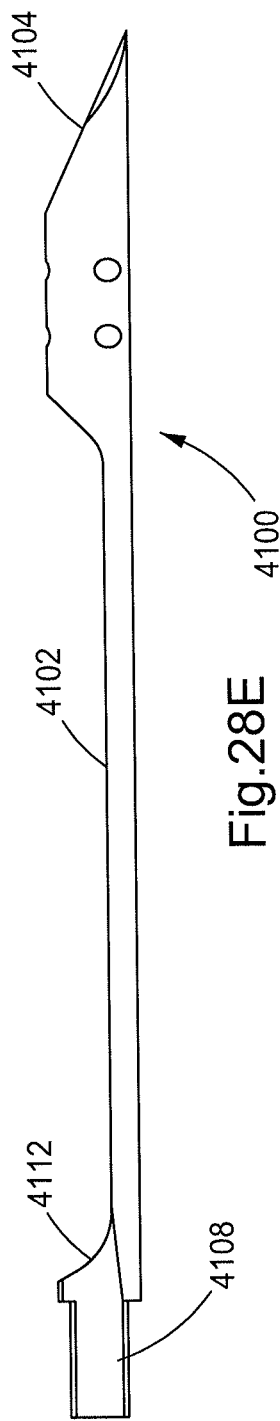
FIG. 28E is a side view of the tissue collection portion of the stylet of FIG. 27A.

FIG. 28A to 28E show a stylet 4000 in accordance with an aspect of the present invention. FIG. 28A shows a perspective view of the stylet 4000. As shown in FIG. 28A, the stylet 4000 may include two portions, a tissue collection portion 4100 and a hollow stylet tube 1002, 2002. When used in the device 1000, the hollow stylet tube 1002, 2002 extends all the way to the rear of the device 1000, and is coupled with the actuator 1006, as show in FIG. 24. Similarly, when used in the device 2000, the hollow stylet tube 1002, 2002 extends toward the rear of the device 2000 and is operatively coupled with the actuator 2006, as shown in FIG. 26. Operation of the actuator and movement of the stylet, among other operational features, is described above with respect to the prior art. FIG. 28B shows a side view of the stylet 4000, with the tissue collection portion 4100 inserted into the hollow stylet tube 1002, 2002. FIGS. 28C to 28E show perspective, top, and side views, respectively, of the tissue collection portion 4100 separate from the hollow stylet tube 1002, 2002. The tissue collection portion 4100 may include a relatively flat elongated reduced thickness portion 4102 that collects the tissue. The reduced thickness portion 4102 serves the same function as in the prior art devices. The tissue collection portion 4100 may include a sharp tip 4104, also serving the same function as in the prior art.

The tissue collection portion 4100 may further include an insertion member 4106 located at the rear end. The insertion member 4106 is inserted into the hollow stylet tube 1002, 2002 of the stylet 4000. As best seen in FIG. 28C, the insertion member 4106 may include substantially flat opposing side portions 4108 and substantially curved opposing top and bottom portions 4110. The curved portions 4110 are curved to match the inside curve of the tube 1002, 2002. The insertion member 4106 is thus inserted into the tube 1002, 2002 and is may be bonded inside of the tube 1002, 2002 via the curved portions 4110, as shown in FIG. 28B. The bonding may be performed in the same manner discussed above. Because the flat side portions 4108 do not contact the inner surface of the tube 1002, 2002 of the stylet, an air flow path is provided. As best seen in FIGS. 28C and 28E, the top curved portion 4110 extends to a lip 4114. The lip 4114 forms part of a ramp 4112 which curves toward the reduced thickness portion 4102. As best seen in FIG. 28A, the lip 4114 abuts the end of the tube 1002, 2002 of the stylet when the insertion member 4106 is inserted therein. Furthermore, as seen in FIG. 28C, the flat portions 4108 are maintained along the sides of the ramp 4114. It has been found that when the above-described features are included in the stylet 4000, the structure focuses the vacuum and avoids sucking tissue into the tube 1002, 2002.

FIG. 29A to 29E show a stylet 5000 in accordance with an aspect of the present invention. FIG. 29A shows a perspective view of the stylet 5000. As shown in FIG. 29A, the stylet 5000 may include two portions, a tissue collection portion 5100 and a hollow stylet tube 1002, 2002. When used in the device 1000, the hollow stylet tube 1002, 2002 extends all the way to the rear of the device 1000, and is coupled with the actuator 1006, as show in FIG. 24. Similarly, when used in the device 2000, the hollow stylet tube 1002, 2002 extends toward the rear of the device 2000 and is operatively coupled with the actuator 2006, as shown in FIG. 26. Operation of the actuator and movement of the stylet, among other operational features, is described above with respect to the prior art. FIG. 29B shows a side view of the stylet 5000, with the tissue collection portion 5100 inserted into the hollow stylet tube 1002, 2002. FIGS. 28C to 28E show perspective, top, and side views, respectively, of the tissue collection portion 5100 separate from the hollow stylet tube 1002, 2002. The tissue collection portion 5100 may include a relatively flat elongated reduced thickness portion 5102 that collects the tissue. The reduced thickness portion 5102 serves the same function as in the prior art devices. The tissue collection portion 5100 may include a sharp tip 5104, also serving the same function as in the prior art.

The tissue collection portion 5100 may further include an insertion member 5106 located at the rear end. The insertion member 5106 is inserted into the hollow stylet tube 1002, 2002 of the stylet 5000. As best seen in FIG. 29C, similar to the aspect shown in FIG. 28C, the insertion member 5106 may include substantially flat opposing side portions 5108 and substantially curved opposing top and bottom portions 5110. In the aspect of FIG. 29C, however, the bottom curved portion may include extending curved edges 5116. The curved portions 5110 and the extending curved edges 5116 are curved to match the inside curve of the tube 1002, 2002. The insertion member 5106 is thus inserted into the tube 1002, 2002 and may be bonded inside of the tube 1002, 2002 via the curved portions 5110, as shown in FIG. 29B. The bonding may be performed in the manner described above. Because the flat side portions 5108 do not contact the inner surface of the tube 1002, 2002 of the stylet, an air flow path is provided. As best seen in FIGS. 29C and 29E, the top curved portion 5110 extends to a lip 5114. The lip 5114 forms part of a ramp 5112 which curves toward the reduced thickness portion 5102. As best seen in FIG. 29A, the lip 5114 abuts the end of the tube 1002, 2002 of the stylet when the insertion member 5106 is inserted therein. Furthermore, as seen in FIG. 29C, the flat portions 5108 are maintained along the sides of the ramp 5112. It has been found that when the above-described features are included in the stylet 5000, the structure focuses the vacuum and avoids sucking tissue into the tube 1002, 2002.

Figure 30A:
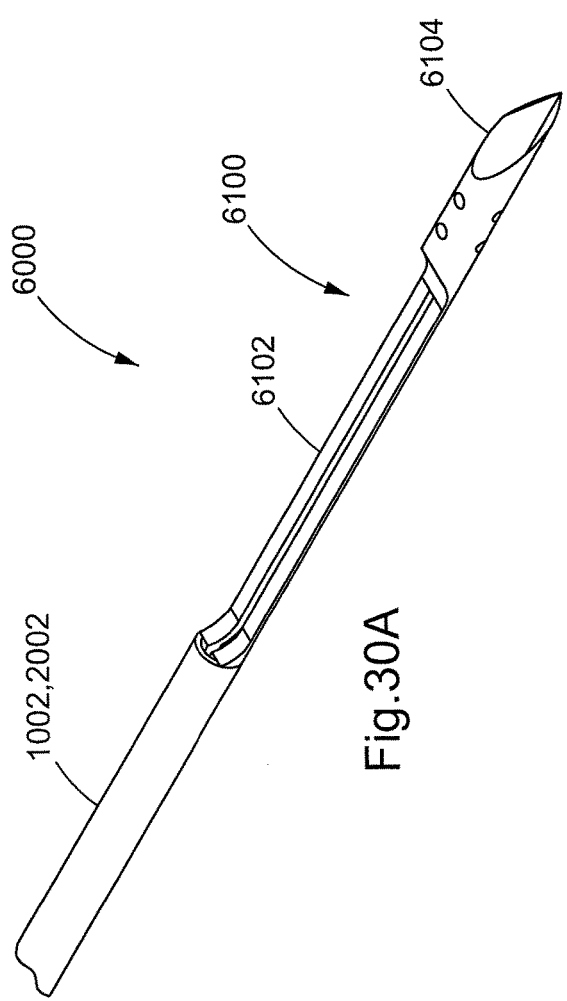
FIGS. 30A is a partial perspective view of a stylet in accordance with other aspects of the present invention.
Figure 30B:
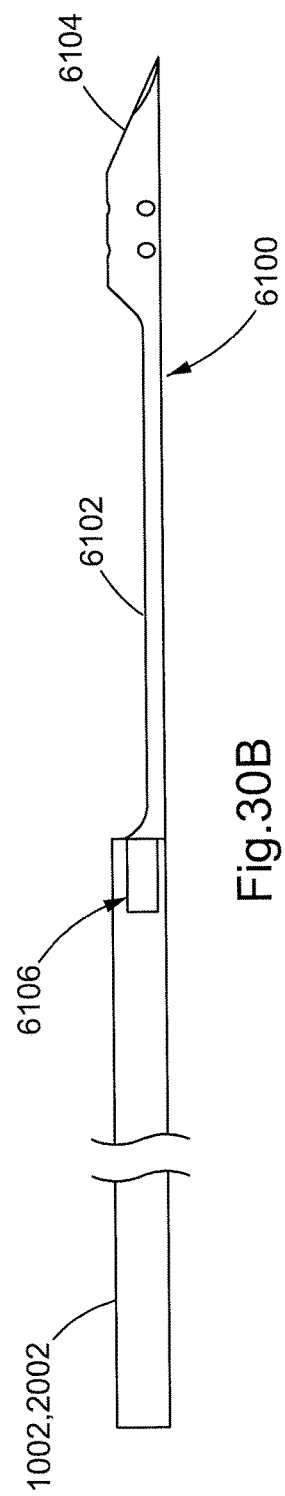
FIG. 30B is a side view of the stylet of FIG. 30A.
Figure 30C:
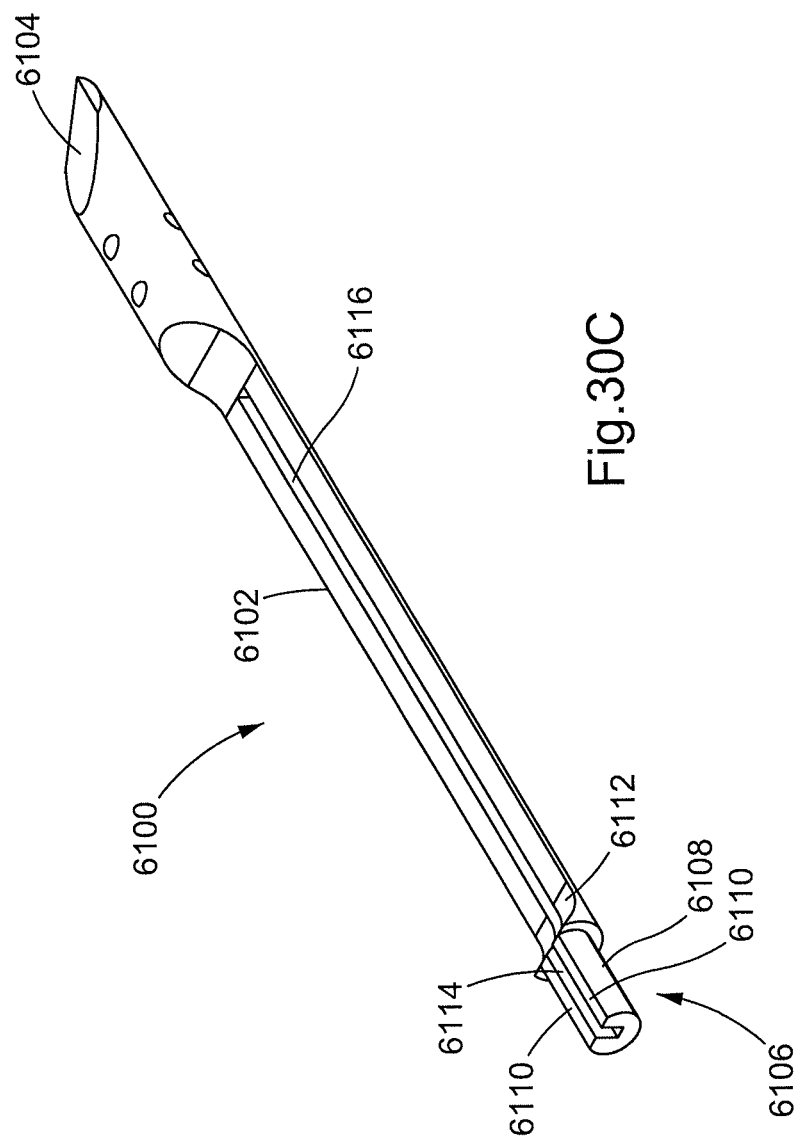
FIG. 30C is a perspective view of the tissue collection portion of the stylet of FIG. 30A.

FIG. 30A to 30E show a stylet 6000 in accordance with an aspect of the present invention. FIG. 30A shows a perspective view of the stylet 6000. As shown in FIG. 30A, the stylet 6000 may include two portions, a tissue collection portion 6100 and a hollow stylet tube 1002, 2002. When used in the device 1000, the hollow stylet tube extends all the way to the rear of the device 1000, and is coupled with the actuator 1006, as show in FIG. 24. Similarly, when used in the device 2000, the hollow stylet tube extends toward the rear of the device 2000 and is operatively coupled with the actuator 2006, as shown in FIG. 26. Operation of the actuator and movement of the stylet, among other operational features, is described above with respect to the prior art. FIG. 30B shows a side view of the stylet 6000, with the tissue collection portion 6100 inserted into the hollow stylet tube 1002, 2002. FIGS. 30C to 30E show perspective, top, and side views, respectively, of the tissue collection portion 6100 separate from the hollow stylet tube 1002, 2002. The tissue collection portion 6100 may include a relatively flat elongated reduced thickness portion 6102 that collects the tissue. The reduced thickness portion 6102 serves the same function as in the prior art devices. The tissue collection portion 6100 may include a sharp tip 6104, also serving the same function as in the prior art.

The tissue collection portion 6100 may further include an insertion member 6106 located at the rear end. The insertion member 6106 is inserted into the hollow stylet tube 1002, 2002 of the stylet 6000. As best seen in FIG. 30C, similar to the aspect shown in FIG. 27C, may include substantially curved portion 6108 and a substantially flat top portion 6110. In the aspect of FIG. 30C, however, the insertion member 6106 may include a passageway 6114 extending along the entire length of the insertion member 6106, thus forming a "block-C" cross section. The curved portion 6108 is curved to match the inside curve of the tube 1002, 2002. The insertion member 6106 is thus inserted into the tube 1002, 2002 and may be bonded inside of the tube 1002, 2002 via the curved portion 6108, as shown in FIG. 30B. The bonding may be performed using the same methods discussed above. As seen in FIGS. 30A, 30B, 30C, and 30D, the reduced thickness portion 6102 may also include a passageway 6116 formed along its entire length. The passageway 6116 of the reduced thickness portion 6102 is aligned with the passageway 6114 of the insertion member 6106, and has the same width, thereby forming a continuous passageway. The combination of the flat portion 6110 and the passageways 6114, 6116 form air flow paths. Passageways 6114 and 6116 also provide a secondary pathway for the vacuum to flow should the primary vacuum pathway (pathway formed by the flat portion 6110) become clogged with tissue. Passageways 6114 and 6116 may be sized to prevent tissue from clogging within the passageways, while providing sufficient vacuum to draw tissue down towards the notched portion. For example, if tissue has been sucked into the primary passageway formed by the flat portion 6110 and the inner curvature of tubing 1002, 2002, the vacuum will still be able to flow via passageways 6114 and 6116 to bias tissue toward the reduced thickness portion 6102. As best seen in FIGS. 30C and 30E, the top flat portion 6110 extends to a ramp 6112 which curves toward the reduced thickness portion 6102. Furthermore, as seen in FIG. 30A, the ramp 6112 has a height smaller than the inside diameter of the stylet tube 1002, 2002, thereby providing the flow path. It has been found that when the above-described features are included in the stylet 6000, the structure focuses the vacuum and avoids sucking tissue into the tube 1002, 2002.

Operation of the devices 1000, 2000 will now be described. The operator generally uses the devices in the same manner that the corresponding prior art devices are operated. Before taking the sample the operator preloads the devices by pulling back on the actuator 1006, 2006. The preloading steps are the same as discussed above with respect to the prior art devices. The vacuum source may be turned on before preloading or after preloading, but before actuating the devices (also referred to herein as "firing"). As discussed above with respect to the prior art devices, the device 1000 is fired by pressing the actuator 1006 toward the body, while the device 2000 is fired by pressing pushbutton 2102. At this point the operator leaves the opening 1012, 2024 open so that the vacuum is in communication with ambient air. As long as the opening 1012, 2024 remains open, the vacuum will draw in ambient air and not from the tissue collection portion 3100, 4100, 5100, 6100 of the stylet 3000, 4000, 5000, 6000. When it is the appropriate time to fire the device, the operator presses on the actuator 1006 in the case of device 1000 or on the pushbutton 2012 in the case of the device 2000. This is the same step as the corresponding prior art devices. However, because the opening 1012, 2024 is positioned on the portion of the actuator 1012 (in the device 1000), or on the pushbutton 2012 (in the device 2000) the same act of firing the devices also closes the opening 1012, 2024. When the opening is closed, the vacuum is no longer in communication with ambient air. Thus, the vacuum now acts on the tissue collection portion 3100, 4100, 5100, 6100 of the stylet 3000, 4000, 5000, 6000. Devices in accordance with the instant application allow the operator to only apply the vacuum at the appropriate time, i.e., when a sample is to be taken. Due to the structure of the stylet 3000, 4000, 5000, 6000, the vacuum suction enhances the sample collection without sucking tissue in to the stylet. Compared to the prior art handheld devices without a vacuum, it was found that up to 80% more tissue was obtained in a single sample.

In another aspect of the invention, the operator may provide the vacuum before or without actuating the device 1000, 2000. In the case of device 1000, the operator may press on the actuator 1006 with enough force to sufficiently to cover the opening 1012, but without enough force to disengage the preloading engagement assembly (see prior art description above for the disengagement assembly). At this point the ambient air passage is closed, but the device has not been fired. This allows the operator to see the tissue being pulled down into the reduced thickness portion of the tissue collection portion prior to sampling. It may also be done to provide more suction time before sampling. Similarly, in the case of the device 2000, the operator may press on the pushbutton 2024 with enough force to sufficiently cover the opening 2012 but without enough force to fire the device.

While the example aspects shown in the figures the insertion member 3106, 4106, 5106, 6106 may include an elongated portion that extends into the stylet tube 1002, 2002, it is within the scope hereof that the elongated portion is omitted entirely. For example, the rear of the tissue collection portion 3100, 4100, 5100, 6100 may directly abut up against the stylet tube 1002, 2002. Thus, the vacuum flow path may still be provided to the tissue collection portion 3100, 4100, 5100, 6100, without the needed for the elongated portion of the insertion member being inserted in the stylet tube. This may be achieved either by bonding the rear of the tissue collection portion directly the end of the stylet tube or by forming the entire stylet as a single piece.

Figure 31A:
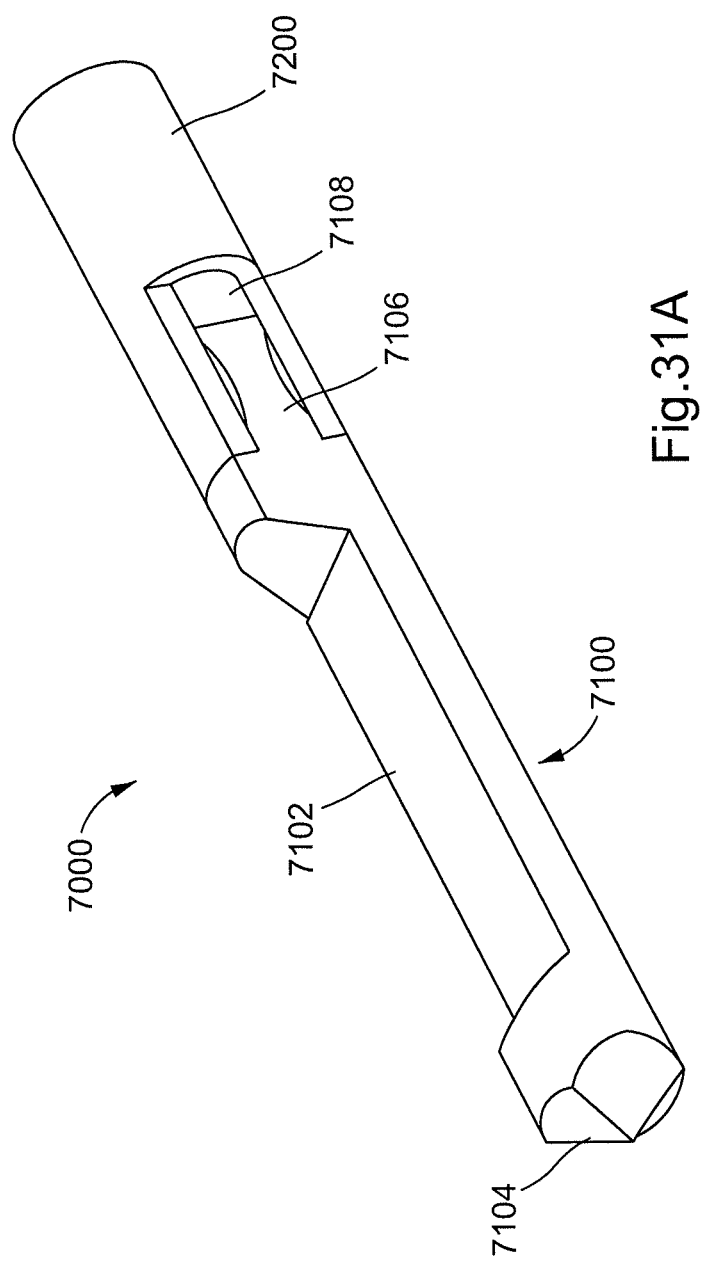
FIG. 31A is a partial perspective view of a stylet in accordance with other aspects of the present invention.

In another aspect of the present invention, the stylet tube may include cutouts or slots cut into the hollow tube to provide additional vacuum flow paths. FIGS. 31A shows a perspective view of a stylet 7000 having cutouts 7108. As shown in FIG. 31A, the stylet 7000 may include two portions, a tissue collection portion 7100 and a hollow stylet tube 7200. FIG. 31 B shows a side view of the stylet 7000, with the tissue collection portion 7100 inserted into the hollow stylet tube 7200. FIGS. 31C shows a top view, of the stylet 7000. The tissue collection portion 7100 may include a relatively flat elongated reduced thickness portion 7102 that collects the tissue. The reduced thickness portion 7102 serves the same function as in the prior art devices. The tissue collection portion 7100 may include a sharp tip 7104, also serving the same function as in the prior art. The tissue collection portion 7100 may include an insertion member 7106 located at the rear end. As shown in FIGS. 31A to 31C, the cutouts 7108 may extend along the length of and behind the insertion member 7106. That is, the portion of the tube 7200 that is cutout is may be approximately equal or greater in length to that of the insertion member 7106. As best seen in FIG. 31C, the cutouts 7108 may be formed on both the lateral portions of the hollow tube 7200. In another aspect, when there is no insertion member present, the cutout may begin at the back end of the tissue collection portion and extend into the hollow tube.

FIGS. 32A shows a perspective view of a stylet 8000 having slots 8108. As shown in FIG. 32A, the stylet 8000 may include two portions, a tissue collection portion 8100 and a hollow stylet tube 8200. FIG. 32B shows a side view of the stylet 8000, with the tissue collection portion 8100 inserted into the hollow stylet tube 8200. FIGS. 32C shows a top view, of the stylet 8000. The tissue collection portion 8100 may include a relatively flat elongated reduced thickness portion 8102 that collects the tissue. The reduced thickness portion 8102 serves the same function as in the prior art devices. The tissue collection portion 8100 may include a sharp tip 8104, also serving the same function as in the prior art. The tissue collection portion 8100 may further include an insertion member (not shown) located at the rear end. As shown in FIGS. 31A to 31C, the slots 8108 may be located along the lateral sides of the hollow tube 7200. As best seen in FIG. 31C, the cutouts 8108 maybe formed on both the lateral portions of the hollow tube 7200. As also seen in FIG. 31C, the slots may be positioned so that the slots do not directly oppose each other.

While the cutouts and slots are shown in FIGS. 31A-32C it should be understood that the cutouts or slots, being part of the hollow tube portion of the stylet, may be included in any of the above-described embodiments. That is the hollow tube portion 1002, 2002 of any of FIGS. 27A-30E may include the cutouts and/or slots.

While the above-described aspects of the present invention use mechanical methods of controlling the vacuum, an electronic version is also within the scope hereof. For example, a button or switch may be triggered to control the vacuum instead of manually covering the ambient air opening.

While this invention has been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

We claim:

1. A vacuum assisted handheld biopsy device comprising:
   a housing;
   a stylet slideable within a cannula, the stylet having a hollow tube portion and a tissue collection portion coupled together, the tissue collection portion including a ramp abutting the hollow tube portion;
   an actuator slideable within the housing for driving at least one of the stylet and the cannula;
   a pushbutton configured to actuate the actuator to release at least one of the stylet and cannula from a preloaded state;
   a vacuum source in communication with the stylet in the preloaded state via a first path; and
   an ambient air opening configured such that the ambient air opening provides communication between an ambient atmosphere and the vacuum source in the preloaded state via a second path,
   wherein the ambient air opening is formed by a surface of the pushbutton such that actuation of the actuator disrupts the communication between the ambient atmosphere and the vacuum source, and
   wherein the hollow tube portion being coupled together with the tissue collection portion is such that the first path is sufficient to provide a vacuum suction from the vacuum source to the tissue collection portion.

2. The vacuum assisted handheld biopsy device of claim 1, configured such that disruption of the communication between the ambient atmosphere and the vacuum source via the second path imparts the vacuum suction from the vacuum source to the tissue collection portion via the first path.

3. The vacuum assisted handheld biopsy device of claim 1,
   wherein the first path is at least partially defined by the ramp.

4. The vacuum assisted handheld biopsy device of claim 3,
   wherein the ramp has a height that is smaller than an inner diameter of the hollow tube portion.

5. The vacuum assisted handheld biopsy device of claim 3,
   wherein ramp comprises opposing flat portions, and
   wherein a space around the flat portions of the ramp at least partially defines the first path.

6. The vacuum assisted handheld biopsy device of claim 3,
wherein the ramp comprises an open passageway at least partially defining the first path.

7. The vacuum assisted handheld biopsy device of claim 3,
wherein the ramp comprises a lip projection abutting the hollow tube portion.

8. The vacuum assisted handheld biopsy device of claim 1,
wherein the tissue collection portion is coupled to the hollow tube portion via an insertion member,
wherein the insertion member comprises a curved portion and a flat portion,
wherein the curved portion is bonded to an inside surface of the hollow tube portion, and
wherein a space between the flat portion and the inside surface of the hollow tube portion at least partially defines the first path.

9. The vacuum assisted handheld biopsy device of claim 1,
wherein the tissue collection portion is coupled to the hollow tube portion via an insertion member,
wherein the insertion member comprises opposing curved portions and opposing flat portions,
wherein the curved portions are bonded to an inside surface of the hollow tube portion, and
wherein a space between the flat portions and the inside surface of the hollow tube portion provides the first path.

10. The vacuum assisted handheld biopsy device of claim 9,
wherein one of the curved portions includes extending curved edges contacting the inside surface of the hollow tube portion.

11. The vacuum assisted handheld biopsy device of claim 1,
wherein the tissue collection portion is coupled to the hollow tube portion via an insertion member, and
wherein the insertion member comprises:
a curved portion bonded to an inside surface of the hollow tube portion, and
an open passageway at least partially defining the first path.

12. The vacuum assisted handheld biopsy device of claim 11,
wherein the tissue collection portion includes a passageway formed therein, and
wherein the passageway of the tissue collection portion is in communication with the passageway of the insertion member.

13. The vacuum assisted handheld biopsy device of claim 1, wherein the second path comprises a pushbutton vacuum tube connected to the pushbutton; and
the first path comprises a stylet vacuum tube connected to the stylet.

14. A method of operating the vacuum assisted handheld biopsy device of claim 1, the method comprising:
preloading the device to the preloaded state;
activating the vacuum source; and
closing the ambient air opening to disrupt the communication between the ambient atmosphere and the vacuum source, wherein closing the ambient air opening directs the vacuum suction along the first path.

15. The method of claim 14, further comprising releasing at least one of the stylet and cannula from the preloaded state contemporaneously with closing the ambient air opening.

16. The method of claim 14, wherein closing the ambient air opening includes pressing the pushbutton.

* * * * *